US010557137B2

United States Patent
Viney et al.

(10) Patent No.: US 10,557,137 B2
(45) Date of Patent: Feb. 11, 2020

(54) MODULATING APOLIPOPROTEIN (A) EXPRESSION

(71) Applicant: Ionis Pharmaceuticals, Inc., Carlsbad, CA (US)

(72) Inventors: Nicholas J. Viney, Carlsbad, CA (US); Richard S. Geary, Carlsbad, CA (US); Yanfeng Wang, Carlsbad, CA (US); Zhengrong Yu, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/772,649

(22) PCT Filed: Nov. 7, 2016

(86) PCT No.: PCT/US2016/060816
§ 371 (c)(1),
(2) Date: May 1, 2018

(87) PCT Pub. No.: WO2017/079739
PCT Pub. Date: May 11, 2017

(65) Prior Publication Data
US 2019/0136233 A1   May 9, 2019

Related U.S. Application Data

(60) Provisional application No. 62/252,392, filed on Nov. 6, 2015.

(51) Int. Cl.
*C12N 15/113* (2010.01)
*A61K 9/08* (2006.01)
*A61J 1/05* (2006.01)
*A61K 9/00* (2006.01)

(52) U.S. Cl.
CPC .............. *C12N 15/113* (2013.01); *A61J 1/05* (2013.01); *A61K 9/0019* (2013.01); *A61K 9/08* (2013.01); *C12N 2310/11* (2013.01); *C12N 2310/315* (2013.01); *C12N 2310/341* (2013.01); *C12N 2310/351* (2013.01); *C12N 2320/32* (2013.01); *C12N 2320/35* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,751,219 A | 6/1988 | Kempen et al. |
| 4,845,205 A | 7/1989 | Huynh Dinh et al. |
| 4,981,957 A | 1/1991 | Lableu et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,198 A | 1/1993 | Spielvogel et al. |
| 5,185,444 A | 2/1993 | Summerton et al. |
| 5,223,618 A | 6/1993 | Cook et al. |
| 5,256,775 A | 10/1993 | Froehler |
| 5,264,562 A | 11/1993 | Matteucci |
| 5,264,564 A | 11/1993 | Matteucci |
| 5,319,080 A | 6/1994 | Leumann |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,432,272 A | 7/1995 | Benner |
| 5,434,257 A | 7/1995 | Matteucci et al. |
| 5,446,137 A | 8/1995 | Maag et al. |
| 5,457,187 A | 10/1995 | Gmelner et al. |

(Continued)

FOREIGN PATENT DOCUMENTS

| CA | 2450022 | 12/2002 |
|---|---|---|
| WO | WO 1994/002499 | 2/1994 |

(Continued)

OTHER PUBLICATIONS

Akinc et al., "Targeted Delivery of RNAi Therapeutics with Endogenous and Exogenous Ligand-Based Mechanisms" Molecular Therapy (2010) 18(7): 1357-1364.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Allshire, "Molecular biology. RNAi and heterochromatin—a hushed-up affair" Science (2002) 297(5588):1818-1819.

Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.

(Continued)

*Primary Examiner* — Sean McGarry
(74) *Attorney, Agent, or Firm* — Grant IP, Inc.

(57) ABSTRACT

Provided herein are oligomeric compounds with conjugate groups targeting apoplipoprotein (a) [apo(a)]. In certain embodiments, the apo(a) targeting oligomeric compounds are conjugated to N-Acetylgalactosamine. Also disclosed herein are conjugated oligomeric compounds targeting apo (a) for use in decreasing apo(a) to treat, prevent, or ameliorate diseases, disorders or conditions related to apo(a) and/or Lp(a). Certain diseases, disorders or conditions related to apo(a) and/or Lp(a) include inflammatory, cardiovascular and/or metabolic diseases, disorders or conditions. The conjugated oligomeric compounds disclosed herein can be used to treat such diseases, disorders or conditions in an individual in need thereof.

10 Claims, 15 Drawing Sheets

Specification includes a Sequence Listing.

(56) References Cited

U.S. PATENT DOCUMENTS

| | | | |
|---|---|---|---|
| 5,459,255 A | 10/1995 | Cook et al. |
| 5,466,786 A | 11/1995 | Buhr et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,134 A | 5/1996 | Acevedo et al. |
| 5,525,711 A | 6/1996 | Hawkins et al. |
| 5,552,540 A | 9/1996 | Hamlambidis |
| 5,567,811 A | 10/1996 | Mistura et al. |
| 5,576,427 A | 11/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |
| 5,597,909 A | 1/1997 | Urdea et al. |
| 5,602,240 A | 2/1997 | De Mesmaeker et al. |
| 5,610,289 A | 3/1997 | Cook et al. |
| 5,610,300 A | 3/1997 | Altmann et al. |
| 5,614,617 A | 3/1997 | Cook et al. |
| 5,625,050 A | 4/1997 | Beaton et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | McGee |
| 5,670,633 A | 9/1997 | Cook et al. |
| 5,681,941 A | 10/1997 | Cook et al. |
| 5,698,685 A | 12/1997 | Summerton et al. |
| 5,700,920 A | 12/1997 | Altmann et al. |
| 5,750,692 A | 5/1998 | Cook et al. |
| 5,763,588 A | 6/1998 | Matteucci et al. |
| 5,792,847 A | 8/1998 | Buhr et al. |
| 5,801,154 A | 9/1998 | Baracchini et al. |
| 5,830,653 A | 11/1998 | Froehler et al. |
| 5,877,022 A | 3/1999 | Stinchcomb et al. |
| 5,994,517 A | 11/1999 | Ts'o et al. |
| 5,998,203 A | 12/1999 | Matulic-Adamic |
| 6,005,096 A | 12/1999 | Matteucci et al. |
| 6,268,490 B1 | 7/2001 | Imanishi et al. |
| 6,300,319 B1 | 10/2001 | Manoharan |
| 6,383,812 B1 | 5/2002 | Chen et al. |
| 6,525,031 B2 | 2/2003 | Manoharan |
| 6,525,191 B1 | 2/2003 | Ramasamy |
| 6,582,908 B2 | 6/2003 | Fodor et al. |
| 6,600,032 B1 | 7/2003 | Manoharan et al. |
| 6,620,916 B1 | 9/2003 | Takahara et al. |
| 6,660,720 B2 | 12/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 7,034,133 B2 | 4/2006 | Wengel et al. |
| 7,053,207 B2 | 5/2006 | Wengel |
| 7,259,150 B2 | 8/2007 | Crooke et al. |
| 7,262,177 B2 | 8/2007 | Ts'o et al. |
| 7,267,819 B2 | 9/2007 | Ferrara et al. |
| 7,399,845 B2 | 7/2008 | Seth et al. |
| 7,427,672 B2 | 9/2008 | Imanishi et al. |
| 7,439,043 B2 | 10/2008 | DeFrees et al. |
| 7,491,805 B2 | 2/2009 | Vargeese et al. |
| 7,569,686 B1 | 8/2009 | Bhat et al. |
| 7,582,744 B2 | 9/2009 | Manoharan et al. |
| 7,598,227 B2 | 10/2009 | Crooke et al. |
| 7,723,509 B2 | 5/2010 | Manoharan et al. |
| 7,741,457 B2 | 6/2010 | Swayze et al. |
| 7,851,615 B2 | 12/2010 | Manoharan et al. |
| 7,935,796 B2 | 5/2011 | Lee et al. |
| 8,106,022 B2 | 1/2012 | Manoharan et al. |
| 8,137,695 B2 | 3/2012 | Rozema et al. |
| 8,138,328 B2 | 3/2012 | Crooke et al. |
| 8,158,601 B2 | 4/2012 | Chen et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,530,640 B2 | 9/2013 | Seth et al. |
| 8,541,376 B2 | 9/2013 | Ferrara et al. |
| 8,541,548 B2 | 9/2013 | Rozema |
| 8,546,556 B2 | 10/2013 | Seth et al. |
| 8,552,163 B2 | 10/2013 | Lee et al. |
| 8,653,047 B2 | 2/2014 | Crooke et al. |
| 8,673,632 B2 | 3/2014 | Crooke et al. |
| 8,742,075 B2 | 6/2014 | Lee et al. |
| 9,127,276 B2 | 9/2015 | Prakash et al. |
| 9,145,558 B2 * | 9/2015 | Prakash ............ A61K 31/7088 |
| 9,163,239 B2 * | 10/2015 | Prakash ............ A61K 31/713 |
| 9,181,550 B2 * | 11/2015 | Prakash ............ A61K 47/549 |
| 9,884,045 B2 * | 2/2018 | Takahashi ............ A61K 31/423 |
| 9,957,505 B2 * | 5/2018 | Hauser .................... C12N 15/111 |
| 10,280,423 B2 * | 5/2019 | Prakash .............. C12N 15/1137 |
| 10,294,477 B2 * | 5/2019 | Swayze ................. C07H 21/00 |
| 2001/0053519 A1 | 12/2001 | Fodor et al. |
| 2003/0017488 A1 | 1/2003 | Koishi et al. |
| 2003/0077829 A1 | 4/2003 | MacLachlan |
| 2003/0119724 A1 | 6/2003 | Ts'o et al. |
| 2003/0170249 A1 | 9/2003 | Hakomori et al. |
| 2003/0228597 A1 | 12/2003 | Cowsert et al. |
| 2004/0171570 A1 | 9/2004 | Allerson et al. |
| 2004/0242516 A1 | 12/2004 | Crooke et al. |
| 2005/0009088 A1 | 1/2005 | Crooke et al. |
| 2005/0130923 A1 | 6/2005 | Bhat et al. |
| 2005/0164235 A1 | 7/2005 | Manoharan et al. |
| 2005/0255487 A1 | 11/2005 | Khvorova et al. |
| 2006/0148740 A1 | 7/2006 | Platenburg |
| 2006/0183886 A1 | 8/2006 | Tso et al. |
| 2007/0031844 A1 | 2/2007 | Khvorova et al. |
| 2007/0054856 A1 | 3/2007 | Gerber et al. |
| 2007/0287831 A1 | 12/2007 | Seth et al. |
| 2008/0039618 A1 | 2/2008 | Allerson et al. |
| 2008/0108801 A1 | 5/2008 | Manoharan et al. |
| 2008/0113351 A1 | 5/2008 | Nalto et al. |
| 2008/0177045 A1 | 7/2008 | Lee et al. |
| 2008/0206869 A1 | 8/2008 | Smith et al. |
| 2008/0255030 A1 | 10/2008 | Yu et al. |
| 2008/0281041 A1 | 11/2008 | Rozema et al. |
| 2008/0281044 A1 | 11/2008 | Manoharan et al. |
| 2009/0012281 A1 | 1/2009 | Swayze et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2009/0306180 A1 | 12/2009 | Bhanot et al. |
| 2009/0318536 A1 | 12/2009 | Freier et al. |
| 2009/0326040 A1 | 12/2009 | Geary et al. |
| 2010/0240730 A1 | 9/2010 | Beigelman et al. |
| 2010/0331390 A1 | 12/2010 | Crooke et al. |
| 2011/0039910 A1 | 2/2011 | Crooke et al. |
| 2011/0077386 A1 | 3/2011 | Lee et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0201798 A1 | 8/2011 | Manoharan et al. |
| 2011/0207799 A1 | 8/2011 | Rozema et al. |
| 2011/0243948 A1 | 10/2011 | Lee et al. |
| 2011/0269814 A1 | 11/2011 | Manoharan et al. |
| 2012/0035115 A1 | 2/2012 | Manoharan et al. |
| 2012/0095075 A1 | 4/2012 | Manoharan et al. |
| 2012/0101148 A1 | 4/2012 | Aking et al. |
| 2012/0122958 A1 | 5/2012 | Dawson et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0183602 A1 | 7/2012 | Chen et al. |
| 2012/0230938 A1 | 9/2012 | Rozema et al. |
| 2013/0004427 A1 | 1/2013 | El-Sayed et al. |
| 2013/0017250 A1 | 1/2013 | Ginsberg et al. |
| 2013/0023579 A1 | 1/2013 | Crooke et al. |

(56) References Cited

U.S. PATENT DOCUMENTS

| | | | |
|---|---|---|---|
| 2013/0109817 A1 | 5/2013 | Yurkovetskiy et al. | |
| 2013/0121954 A1 | 5/2013 | Wakefield et al. | |
| 2013/0178512 A1 | 7/2013 | Manoharan et al. | |
| 2013/0236968 A1 | 9/2013 | Manoharan et al. | |
| 2013/0281511 A1 | 10/2013 | Bettencourt et al. | |
| 2013/0317085 A1 | 11/2013 | Crooke et al. | |
| 2014/0343123 A1 | 11/2014 | Prakash et al. | |
| 2015/0057329 A1 | 2/2015 | Bhanot et al. | |
| 2015/0126719 A1 | 5/2015 | Prakash et al. | |
| 2015/0126720 A1 | 5/2015 | Prakash et al. | |
| 2018/0256629 A1* | 9/2018 | Crooke | C12N 15/113 |

FOREIGN PATENT DOCUMENTS

| | | |
|---|---|---|
| WO | WO 1994/017093 | 8/1994 |
| WO | WO 1997/020563 | 6/1997 |
| WO | WO 1997/046098 | 12/1997 |
| WO | WO 1998/013381 | 4/1998 |
| WO | WO 1998/039352 | 9/1998 |
| WO | WO 1999/014226 | 3/1999 |
| WO | WO 2000/014048 | 3/2000 |
| WO | WO 2000/063364 | 10/2000 |
| WO | WO 2001/005825 | 1/2001 |
| WO | WO 2001/049687 | 7/2001 |
| WO | WO 2002/043771 | 6/2002 |
| WO | WO 2003/004602 | 1/2003 |
| WO | WO 2003/014397 | 2/2003 |
| WO | WO 2003/044172 | 5/2003 |
| WO | WO 2004/035765 | 10/2003 |
| WO | WO 2004/024757 | 3/2004 |
| WO | WO 2004/044181 | 5/2004 |
| WO | WO 2004/063208 | 7/2004 |
| WO | WO 2004/093783 | 11/2004 |
| WO | WO 2004/101619 | 11/2004 |
| WO | WO 2004/106356 | 12/2004 |
| WO | WO 2005/000201 | 1/2005 |
| WO | WO 2005/021570 | 3/2005 |
| WO | WO 2005/097155 | 10/2005 |
| WO | WO 2005/121371 | 12/2005 |
| WO | WO 2006/031461 | 3/2006 |
| WO | WO 2006/047842 | 5/2006 |
| WO | WO 2007/035759 | 3/2007 |
| WO | WO 2007/090071 | 8/2007 |
| WO | WO 2007/134181 | 11/2007 |
| WO | WO 2008/073300 | 6/2008 |
| WO | WO 2008/098788 | 8/2008 |
| WO | WO 2008/101157 | 8/2008 |
| WO | WO 2008/150729 | 12/2008 |
| WO | WO 2008/154401 | 12/2008 |
| WO | WO 2009/003009 | 12/2008 |
| WO | WO 2009/006478 | 1/2009 |
| WO | WO 2009/073809 | 6/2009 |
| WO | WO 2009/082607 | 7/2009 |
| WO | WO 2009/126933 | 10/2009 |
| WO | WO 2009/134487 | 11/2009 |
| WO | WO 2009/143369 | 11/2009 |
| WO | WO 2010/036696 | 4/2010 |
| WO | WO 2010/036698 | 4/2010 |
| WO | WO 2010/048549 | 4/2010 |
| WO | WO 2010/048585 | 4/2010 |
| WO | WO 2010/054406 | 5/2010 |
| WO | WO 2010/077578 | 7/2010 |
| WO | WO 2010/083615 | 7/2010 |
| WO | WO 2010/088537 | 8/2010 |
| WO | WO 2010/101951 | 9/2010 |
| WO | WO 2010/103204 | 9/2010 |
| WO | WO 2010/129709 | 11/2010 |
| WO | WO 2010/144740 | 12/2010 |
| WO | WO 2010/148013 | 12/2010 |
| WO | WO 2011/005860 | 1/2011 |
| WO | WO 2011/005861 | 1/2011 |
| WO | WO 2011/038356 | 3/2011 |
| WO | WO 2011/085271 | 7/2011 |
| WO | WO 2011/100131 | 8/2011 |
| WO | WO 2011/115818 | 9/2011 |
| WO | WO 2011/120053 | 9/2011 |
| WO | WO 2011/133871 | 10/2011 |
| WO | WO 2011/139702 | 10/2011 |
| WO | WO 2011/163121 | 12/2011 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/135736 | 10/2012 |
| WO | WO 2012/145674 | 10/2012 |
| WO | WO 2012/145697 | 10/2012 |
| WO | WO 2012/149495 | 11/2012 |
| WO | WO 2012/177784 | 12/2012 |
| WO | WO 2012/177947 | 12/2012 |
| WO | WO 2013/033230 | 3/2013 |
| WO | WO 2013/075035 | 5/2013 |
| WO | WO 2013/119979 | 8/2013 |
| WO | WO 2013/142571 | 9/2013 |
| WO | WO 2013/165816 | 11/2013 |
| WO | WO 2013/166121 | 11/2013 |
| WO | WO 2013/173789 | 11/2013 |
| WO | WO 2013/177468 | 11/2013 |
| WO | WO 2014/076195 | 5/2014 |
| WO | WO 2014/076196 | 5/2014 |
| WO | WO 2014/118267 | 8/2014 |
| WO | WO 2014/118272 | 8/2014 |
| WO | WO 2014/179620 | 11/2014 |
| WO | WO 2014/179625 | 11/2014 |
| WO | WO 2014/179626 | 11/2014 |
| WO | WO 2014/179627 | 11/2014 |
| WO | WO 2014/179629 | 11/2014 |
| WO | WO 2014/205451 | 12/2014 |
| WO | WO 2014/207232 | 12/2014 |
| WO | WO 2015/168589 | 11/2015 |
| WO | WO 2017/079745 | 5/2017 |

OTHER PUBLICATIONS

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure—activity relationships and the design of improved signal-transduction inhibitors" Biochem. Soc. Trans. (1996) 24:630-637.

Ando et al, "A decreased expression of angiopoietin-like 3 is protective against atherosclerosis in apoE-deficient mice" J Lipid Res. (2003) 44(6):1216-23.

Andre et al., "Determination of modulation of ligand properties of synthetic complex-type biantennary N-glycans by introduction of bisecting GlcNAc in silico, in vitro and in vivo" Eur. J. Biochem. (2004) 271: 118-134.

Angelakopoulou et al., "Comparative analysis of genome-wide association studies signals for lipids, diabetes, and coronary heart disease: Cardiovascular Biomarker Genetics Collaboration" Eur Heart J. (2012) 33(3):393-407.

Asseline et al., "Modification of the 5' Terminus of Oligodeoxyribonucleotides for Conjugation with Ligands" in Current Protocols in Nucleic Acid Chemistry, 2001, Supplement 5, Chapter 4: Unit 4.9 (4.9.1-4.9.28); John Wiley & Sons.

Atsma et al., "Partial characterization of low density lipoprotein preparations isolated from fresh and frozen plasma after radiolabeling by seven different methods." J Lipid Res. (1991) 32(1): 173-181.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Beaucage et al., "The functionalization of oligonucleotides via phosphoramidate derivatives" Tetrahedron (1993) 49(10): 1925-1963.

Bergmark et al., "A novel function of lipoprotein [a] as a preferential carrier of oxidized phospholipids in human plasma" J Lipid Res (2008) 49(10): 2230-2239.

(56) References Cited

OTHER PUBLICATIONS

Biessen et al., "Novel hepatotrophic prodrugs of the antiviral nucleoside 9-(2-phosphonylmethoxyethyl)adenine with improved pharmacokinetics and antiviral activity" FASEB J. (2000) 14: 1784-1792.
Biessen et al., "Synthesis of Cluster Galactosides with High Affinity for the Hepatic Asialoglycoprotein Receptor" J. Med. Chem. (1995) 38:1538-1546.
Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.
Bligh et al., "A rapid method of total lipid extraction and purification" Can. J. Biochem. Physiol. (1959) 37(8):911-917.
Braasch et al., "Locked nucleic acid (LNA): fine-tuning the recognition of DNA and RNA" Chem. Biol. (2001) 8:1-7.
Braasch et al., "Novel Antisense and Peptide Nucleic Acid Strategies for Controlling Gene Expression" Biochemistry (2002) 41(14): 4503-4510.
Branch et al., "A good antisense molecule is hard to find," TIBS (1998) 23:45-50.
Branda et al., "Amplification of antibody production by phosphorothioate oligodeoxynucleotides" J Lab Clin Med. (1996) 128(3): 329-338.
Browning et al., "Molecular mediators of hepatic steatosis and liver injury" J. Clin. Invest. (2004) 114(2):147-152.
Camenisch et al., "ANGPTL3 stimulates endothelial cell adhesion and migration via integrin alpha vbeta 3 and induces blood vessel formation in vivo." J. Biol. Chem. (2002) 277(19):17281-17290.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Clarke et al., "Genetic variants associated with Lp(a) lipoprotein level and coronary disease" N Engl J Med (2009) 361(26): 2518-2528.
Coltart et al., "Principles of Mucin Architecture: Structural Studies on Synthetic Glycopeptides Bearing Clustered Mono-, Di-, Tri-, and Hexasaccharide Glycodomains" J. Am. Chem. Soc. (2002) 124: 9833-9844.
Conklin et al., "Identification of a mammalian angiopoietin-related protein expressed specifically in liver." Genomics (1999) 62(3):477-482.
Connolly et al., "Binding and Endocytosis of Cluster Glycosides by Rabbit Hepatocytes" J Biol Chem (1982) 257: 939-945.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Crooke et al., "Pharmacological Properties of 2'-O-Methoxyethyl Modified Oligonucleotides" in Antisense a Drug Technology, Chapter 10, pp. 273-303, Crooke, S.T., ed., 2008.
Crooke et al., "Toxicologic Properties of 2 -O-Methoxyethyl Chimeric Antisense Inhibitors in Animals and Man" in Antisense a Drug Technology, Chapter 12, pp. 342-351, Crooke, S.T., ed., 2008.
Czech et al. "RNAi-based therapeutic strategies for metabolic disease" Nature Reviews Endocrinology (2011) 7:473-484.
Davidson et al., "Apolipoprotein B: mRNA Editing, Lipoprotein Assembly, and Presecretory Degradation" Annu. Rev. Nutr. (2000) 20: 169-193.
Dellinger et al., "Solid-Phase Chemical Synthesis of Phosphonoacetate and Thiophosphonoacetate Oligodeoxynucleotides" J. Am .Chem. Soc. (2003) 125: 940-950.
Duff et al., "Intrabody Tissue-Specific Delivery of Antisense Conjugates in Animals. Ligand-Linker-Antisense Oligomer Conjugates" Methods in Enzymology (1999) 313: 297-321.
Dupouy et al., "Watson—Crick Base-Pairing Properties of Nucleic Acid Analogues with Stereocontrolled a and b Torsion Angles (a,b-D-CNAs)" Angew. Chem. Int. Ed. (2006) 45: 3623-3627.

Elayadi et al., "Application of PNA and LNA oligomers to chemotherapy" Curr. Opinion Invens. Drugs (2001) 2:558-561.
EMBL Accession No. BG400407, *Homo sapiens* cDNA clone, Mar. 17, 2001, retrieved from the Internet, Apr. 3, 2013 <http://www.ebi.ac.uk/Tools/dbfetch/emblfetch?id—BG400407&Submit=Go>.
Englisch et al., "Chemically Modified Oligonucleotides as Probes and Inhibitors" Agnew Chem. Int. Ed. Engl. (1991) 30:613-629.
Erqou et al., "Lipoprotein(a) concentration and the risk of coronary heart disease, stroke, and nonvascular mortality" JAMA (2009) 302(4): 412-423.
European Search Report for application EP 11732249.5 dated Aug. 7, 2014.
Expert Panel on Detection, Evaluation, and Treatment of High Blood Cholesterol in Adults. "Executive Summary of The Third Report of The National Cholesterol Education Program (NCEP) Expert Panel on Detection, Evaluation, And Treatment of High Blood Cholesterol In Adults (Adult Treatment Panel III)" JAMA. (2001) 285(18):2486-2497.
Fredrickson et al., "A System for Phenotyping Hyperlipoproteinemia" Circulation (1965) 31: 321-327.
Fredrickson et al., "Fat transport in lipoproteins—an integrated approach to mechanisms and disorders" N Engl J Med (1967) 276: 34-42.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fujimoto et al., "Angptl3 -null mice show low plasma lipid concentrations by enhanced lipoprotein lipase activity" Exp. Anim. (2006) 55(1):27-34.
Gao et al., "Angiopoietin-like protein 3 regulates the motility and permeability of podocytes by altering nephrin expression in vitro" Biochemical and Biophysical Research Communications (2010) 399: 31-36.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.
Geary et al., "A nonradioisotope biomedical assay for intact oligonucleotide and its chain-shortened metabolites used for determination of exposure and elimination half-life of antisense drugs in tissue" Anal. Biochem. (1999) 274(2):241-248.
Geary et al., "Pharmacokinetic Properties of 2'-O-(2-Methoxyethyl)-Modified Oligonucleotide Analogs in Rats" The Journal of Pharmacology and Experimental Therapeutics (2001) 296:890-897.
GenBank Accession No. NM_014495.3. *Homo sapiens* angiopoietin-like 3 (ANGPTL3) mRNA, retrieved from the Internet on Apr. 18, 2013, downloaded from http://www.ncbi.nlm.nih.gov/nuccore/NM_014495.1.
Goodman et al., "Report of the National Cholesterol Education Program Expert Panel on Detection, Evaluation, and Treatment of High Blood Cholesterol in Adults. The Expert Panel" Arch Intern Med (1988) 148:36-39.
Graham et al., "Antisense oligonucleotide inhibition of apolipoprotein C-III reduces plasma triglycerides in rodents, nonhuman primates, and humans" Circ. Res. (2013) 112(11):1479-1490.
Gu et al., "Base pairing properties of D- and L-cyclohexene nucleic acids (CeNA)" Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Guzaev et al., "A conformationally preorganized universal solid support for efficient oligonucleotide synthesis" J. Am. Chem. Soc. (2003) 125(9):2380-2381.
Hall et al., "Establishment and maintenance of a heterochromatin domain" Science (2002) 297(5590):2232-2237.
Hanessian et al., "Synthesis of chemically and functionally diverse scaffolds from pentaerythritol" Canadian Journal of Chemistry (1996) 74(9):1731-1737.

(56) References Cited

OTHER PUBLICATIONS

Hatsuda et al., "Association between Plasma Angiopoietin-Like Protein 3 and Arterial Wall Thickness in Healthy Subjects" J Vasc Res (2007) 44:61-66.
Hoffman et al., "'Brain-type' N-glycosylation of asialo-transferrin from human cerebrospinal fluid" FEBS Letters (1995) 359: 164-168.
Hooper et al., "Recent developments in the genetics of LDL deficiency" Curr Opin Lipidol (2013) 24(2):111-115.
Horn et al., "Chemical synthesis and characterization of branched oligodeoxyribonucleotides (bDNA) for use as signal amplifiers in nucleic acid quantification assays." Nucleic Acids Research (1997) 25: 4842-4849.
Horvath et al., "Stereoselective synthesis of (−)-ara-cyclohexenyl-adenine" Tetrahedron Letters (2007) 48:3621-3623.
Ichimura et al., "Serum Angiopoietin-like Protein 3 Levels: Possible Correlation with Progressive Skin Sclerosis, Digital Ulcers and Pulmonary Vascular Involvement in Patients with Systemic Sclerosis" Acta Derma Venereol (2013) 1-6.
Inaba et al., "Angiopoietin-like protein 3 mediates hypertriglyceridemia induced by the liver X receptor." J. Biol. Chem. (2003) 278(24):21344-21351.
Inukai et al., "ANGPTL3 is increased in both insulin-deficient and -resistant diabetic states." Biochem. Biophys. Res. Commun. (2004) 317(4):1075-1079.
Ishibashi et al., "Hypercholesterolemia in low density lipoprotein receptor knockout mice and its reversal by adenovirus-mediated gene delivery." J. Clin. Invest. (1993) 92(2):883-893.
Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.
Jenuwein, "Molecular biology. An RNA-guided pathway for the epigenome" Science (2002) 297(5590):2215-2218.
Jiang et al., "The Design and Synthesis of Highly Branched and Spherically Symmetric Fluorinated Oils and Amphiles." Tetrahedron (2007) 63(19): 3982-3988.
Jin et al., "Use of α-N,N-bis[Carboxymethyl]lysine-Modified Peroxidase in Immunoassays" Analytical Biochemistry (1995) 229: 54-60.
Jones et al., "RNA quantitation by fluorescence-based solution assay: RiboGreen reagent characterization" Anal. Biochem. (1998) 265(2):368-374.
Kamstrup et al., "Extreme lipoprotein(a) levels and risk of myocardial infarction in the general population: the Copenhagen City Heart Study" Circulation (2008) 117(2): 176-184.
Kanasty et al., "Delivery Materials for siRNA Therapeutics" Nature Materials (2013) 12: 967-977.
Kaplan et al., "Regulation of the angiopoietin-like protein 3 gene by LXR" J. Lipid Res. (2003) 44(1):136-143.
Kassim et al., "Gene therapy for dyslipidemia: a review of gene replacement and gene inhibition strategies" Clinical Lipidology (2010) 5(6): 793-809.
Kato et al., "N-acetylgalactosamine incorporation into a peptide containing consecutive threonine residues by UDP-N-acetyl-D-galactosaminide:polypeptide N-acetylgalactosaminyltransferases" Glyobiology (2001) 11: 821-829.
Khorev et al., "Trivalent, Gal/GalNAc-containing ligands designed for the asialoglycoprotein receptor" Bioorganic & Medicinal Chemistry (2008) 16: 5216-5231.
Kim et al., "Oligomeric Glycopeptidomimetics Bearing the Cancer Related TN-Antigen" Tetrahedron Letters (1997) 38(20): 3487-3490.
Kim et al., "Synthesis of Novel Phosphoramidite Building Blocks from Pentaerythritol" Synlett (2003) 12: 1838-1840.
Koishi et al., "Angptl3 regulates lipid metabolism in mice" Nat. Genet. (2002) 30(2):151-157.
Koller et al., "Mechanisms of single-stranded phosphorothioate modified antisense oligonucleotide accumulation in hepatocytes." Nucleic Acids Res. (2011) 39(11): 4795-4807.

Kornilova et al., "Development of a fluorescence polarization binding assay for asialoglycoprotein receptor" Analytical Biochemistry (2012) 425: 43-46.
Korstanje et al., "Locating Ath8, a locus for murine atherosclerosis susceptibility and testing several of its candidate genes in mice and humans" Atherosclerosis (2004) 177:443-450.
Koschinsky et al., "Structure-function relationships in apolipoprotein(a): insights into lipoprotein(a) assembly and pathogenicity" Curr Opin Lipidol (2004) 15(2): 167-174.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Koster et al., "Transgenic angiopoietin-like (angptl)4 overexpression and targeted disruption of angptl4 and angptl3: regulation of triglyceride metabolism" Endocrinology (2005) 146(11):4943-50.
Kraft et al., "Frequency distributions of apolipoprotein(a) kringle IV repeat alleles and their effects on lipoprotein(a) levels in Caucasian, Asian, and African populations: the distribution of null alleles is non-random" Eur J Hum Genet (1996) 4(2): 74-87.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Lazaris-Karatzas et al., "Malignant transformation by a eukaryotic initiation factor subunit that binds to mRNA 5' cap" Nature (1990) 345: 544-547.
Lee et al., "Synthesis of some cluster glycosides suitable for attachment to proteins or solid matrices" Carbohydrate Research (1978) 67: 509-514.
Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)" Journal of Biological Chemistry (2009) 284(20): 13735-13745.
Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.
Lee et al., "New and more efficient multivalent glyco-ligands for asialoglycoprotein receptor of mammalian hepatocytes" Bioorganic & Medicinal Chemistry (2011) 19:2494-2500.
Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.
Lee et al., "Synthesis of Peptide-Based Trivalent Scaffold for Prepamtion of Cluster Glycosides" Methods in Enzymology (2003) 362: 38-43.
Lee et al., "New synthetic cluster ligands for galactose/N-acetylgalactosamine-specific lectin of mammalian liver" Biochem (1984) 23: 4255-4261.
Lee et al., "Protein microarrays to study carbohydrate-recognition events" Bioorg Med Chem Lett (2006) 16(19): 5132-5135.
Lee et al., "Synthesis of multivalent neoglycoconjugates of MUC1 by the conjugation of carbohydrate-centered, triazole-linked glycoclusters to MUC1 peptides using click chemistry." J Org Chem (2012) 77: 7564-7571.
Lee et al., "Antisense Technology: An Emerging Platform for Cardiovascular Disease Therapeutics" J of Cardiovasc Trans Res (2013) 6: 969-980.
Leeds et al., "Quantitation of phosphorothioate oligonucleotides in human plasma" Anal. Biochem. (1996) 235(1):36-43.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.

(56) References Cited

OTHER PUBLICATIONS

Lichtenstein et al., "Modulation of plasma TG lipolysis by Angiopoietin-like proteins and GPIHBP1" Biochimica and Biophysica Acta (2010) 1801(4): 415-420.
Link, "Pharmacological regulation of hepatic glucose production" Curr Opin Investig Drugs (2003) 4: 421-429.
Linton et al., "Transgenic mice expressing high plasma concentrations of human apolipoprotein B100 and lipoprotein(a)." J. Clin. Invest. (1993) 92: 3029-3037.
Lippi et al., "Screening and therapeutic management of lipoprotein(a) excess: review of the epidemiological evidence, guidelines and recommendations" Clinica Chimica Acta (2011) 412: 797-801.
Machida et al., "Bivalent inhibitors for disrupting protein surface-substrate interactions and for dual inhibition of protein prenyltransferases" J. Am. Chem. Soc. (2011) 133(4):958-963.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
Maier et al., "Synthesis of Antisense Oligonucleotides Conjugated to a Multivalent Carbohydrate Cluster for Cellular Targeting" Bioconjugate Chem. (2003) 14: 18-29.
Maierhofer et al., "Probing multivalent carbohydrate-lectin interactions by an enzyme-linked lectin assay employing covalently immobilized carbohydrates" Bioorganic & Medicinal Chemistry (2007) 15: 7661-7676.
Makino et al., "Intravenous Injection with Antisense Oligodeoxynucleotides Against Angiotensinogen Decreases Blood Pressure in Spontaneously Hypertensive RatS" Hypertension (1998) 31: 1166-1170.
Manoharan et al., "Chemical Modifications to Improve Uptake and Bioavailability of Antisense Oligonucleotides" Ann. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "N-(2-Cyanoethoxycarbonyloxy)succinimide: A New Reagent for Protection of Amino Groups in Oligonucleotides" J. Org. Chem. (1999) 64: 6468-6472.
Manoharan et al., "Oligonucleotide Conjugates: Alteration of the Pharmacokinetic Properties of Antisense Agents" Nucleosides & Nucleotides (1995) 14(3-5):969-973.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.
Marcaurelle et al., "Synthesis of Oxime-Linked Mucin Mimics Containing the Tumor-Related TN and Sialyl TN Antigens" Organic Letters (2001) 3(23): 3691-3694.
Martin, "New acces to 2'-O-alkylated ribonucleosides and properties of 2'-O-alkylated oligoribonucleotides" Helv. Chim. Acta. (1995) 78:486-504.
Martin-Campos et al., "Identification of a novel mutation in the ANGPTL3 gene in two families diagnosed of familial hypobetalipoproteinemia without APOB mutation" Clin. Chim. Acta. (2012) 413(5-6):552-555.
Merki et al., "Antisense oligonucleotide lowers plasma levels of apolipoprotein (a) and lipoprotein (a) in transgenic mice" J Am Coll Cardiol (2011) 57(15): 1611-1621.
Merwin et al., "Targeted delivery of DNA using YEE(GalNAcAH)3, a synthetic glycopeptide ligand for the asialoglycoprotein receptor." Bioconjug Chem (1994) 5(6): 612-620.
Minicocci et al., "Clinical characteristics and plasma lipids in subjects with familial combined hypolipidemia: a pooled analysis" J. Lipid Res. (2013) 54(12):3481-3490.
Minicocci et al., "Mutations in the ANGPTL3 gene and familial combined hypolipidemia: a clinical and biochemical characterization" J. Clin. Endocrinol. Metab. (2012) 97(7):E1266-E1275.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Musunuru et al., "Exome sequencing, ANGPTL3 mutations, and familial combined hypolipidemia" N Engl J Med (2010) 363(23):2220-7.
Naoumova et al., "A new drug target for treatment of dyslipidaemia associated with type 2 diabetes and the metabolic syndrome?" Lancet (2002) 359(9325):2215-6.
Nauwelaerts et al., "Cyclohexenyl nucleic acids: conformationally flexible oligonucleotides" Nucleic Acids Res. (2005) 33(8):2452-2463.
Nauwelaerts et al., "Structural characterization and biological evaluation of small interfering RNAs containing cyclohexenyl nucleosides" J. Am. Chem. Soc. (2007) 129(30):9340-9348.
New England Biolabs 1998/99 Catalog (cover page and pp. 121 and 284).
Noto et al., "Prevalence of ANGPTL3 and APOB gene mutations in subjects with combined hypolipidemia" Arterioscler. Thromb. Vasc. Biol. (2012) 32(3):805-809.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Pal-Bhadra et al., "Heterochromatic silencing and HP1 localization in *Drosophila* are dependent on the RNAi machinery" Science (2004) 303(5658):669-672.
Park et al., "The asialoglycoprotein receptor clears glycoconjugates terminating with sialic acid a2,6GalNAc" PNAS (2005) 102(47): 17125-17129.
Pavia et al., "Synthetic TN glycopeptide related to human glycophorin AM. High-field proton and carbon-13 nuclear magnetic resonance study." Int J Pep Protein Res (1983) 22: 539-548.
Petrova et al., "Carrier-free cellular uptake and the gene-silencing activity of the lipophilic siRNAs is strongly affected by the length of the linker between siRNA and lipophilic group" Nucleic Acids Research (2012) 40(5): 2330-2344.
Pisciotta et al., "Characterization of three kindreds with familial combined hypolipidemia caused by loss-of-function mutations of ANGPTL3" Circ. Cardiovasc. Genet. (2012) 5(1):42-50.
Pujol et al., "A Sulfur Tripod Glycoconjugate that Releases a High-Affinity Copper Chelator in Hepatocytes" Angew. Chem. Int. Ed. (2012) 51: 7445-7448.
Rajur et al., "Covalent Protein-Oligonucleotide Conjugates for Efficient Delivery of Antisense Molecules" Bioconjugate Chem. (1997) 8: 935-940.
Raouane et al., "Synthesis, Characterization, and in Vivo Delivery of siRNA-Squalene Nanoparticles Targeting Fusion Oncogene in Papillary Thyroid Carcinoma" J. Med. Chem. (2011) 54: 4067-4076.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.
Rensen et al., "Stimulation of Liver-Directed Cholesterol Flux in Mice by Novel N-Acetylgalactosamine—Terminated Glycolipids With High Affinity for the Asialoglycoprotein Receptor" Arterioscler Thromb Vasc Biol (2006) 26: 169-175.
Reynolds et al., "Rational siRNA design for RNA interference" Nature Biotechnology (2004) 22(3):326-330.

(56) References Cited

OTHER PUBLICATIONS

Rifai et al., "Apolipoprotein(a) size and lipoprotein(a) concentration and future risk of angina pectoris with evidence of severe coronary atherosclerosis in men: The Physicians' Health Study" Clin Chem (2004) 50(8): 1364-1371.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Romeo et al., "Rare loss-of-function mutations in ANGPTL family members contribute to plasma triglyceride levels in humans" J. Clin. Invest. (2009) 119(1):70-79.
Rossenberg et al., "Stable polyplexes based on arginine-containing oligopeptides for in vivo gene delivery" Gene Therapy (2004) 11: 457-464.
Rouchaud et al., "A New and Efficient Synthesis of Derivatives of Octahydro-4H-pyrrolo[1,2-c]pyrido[1',2'-a]imidazole" Eur. J. Org. Chem. (2011) 12: 2346-2353.
Sanan et al., "Low density lipoprotein receptor-negative mice expressing human apolipoprotein B-100 develop complex atherosclerotic lesions on a chow diet: No accentuation by apolipoprotein(a)" PNAS (1998) 95:4544-4549.
Sanghvi et al., "Heterocyclic Base Modifications in Nucleic Acids and Their Applications in Antisense Oligonucleotides" Antisense Research and Applications (1993) pp. 273-288.
Sanghvi, Chapter 15, Antisense Research and Applications, Crooke and Lebleu ed., CRC Press (1993).
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Schultz et al., "Effects of inhibition of interleukin-6 signalling on insulin sensitivity and lipoprotein (a) levels in human subjects with rheumatoid diseases" PLoS One (2010) 5(12): 1-7.
Seth et al., "Synthesis and biophysical characterization of R-6'-Me-α-L-LNA modified oligonucleotides." Bioorg. Med. Chem. (2011) 21(4): 1122-1125.
Seth et al., "Synthesis and Biophysical Evaluation of 2',4'-Constrained 2'O-Methoxyethyl and 2',4'-Constrained 2'O-Ethyl Nucleic Acid Analogues" J Org Chem. (2010) 75(5): 1569-1581.
Seth et al., "Design, Synthesis And Evaluation Of Constrained Methoxyethyl (cMOE) and Constrained Ethyl (cEt) Nucleoside Analogs" Nucleic Acids Symposium Series (2008) 52(1): 553-554.
Shchepinov et al., "Oligonucleotide dendrimers: synthesis and use as polylabelled DNA probes." Nucleic Acids Research (1997) 25(22): 4447-4454.
Shchepinov et al., "Oligonucleotide dendrimers: stable nanostructures" Nucleic Acids Research (1999) 27(15): 3035-3041.
Shea et al., "Synthesis, hybridization properties and antiviral activity of lipid-oligodeoxynucleotide conjugates" Nucl. Acids Res. (1990) 18(13):3777-3783.
Shimamura et al., "" Biochem. Biophys. Res. Commun. (2003) 301:604-609.
Shimamura et al., "Angiopoietin-like protein3 regulates plasma HDL cholesterol through suppression of endothelial lipase" Arterioscler Thromb Vasc Biol. (2007) 27(2):366-72.
Shimamura et al., "Leptin and insulin down-regulate angiopoietin-like protein 3, a plasma triglyceride-increasing factor" Biochem. Biophys. Res. Commun. (2004) 322(3):1080-1085.
Shimizugawa et al., "ANGPTL3 decreases very low density lipoprotein triglyceride clearance by inhibition of lipoprotein lipase" J. Biol. Chem. (2002) 277:33742-33748.
Sindelka et al., "Association of obesity, diabetes, serum lipids and blood pressure regulates insulin action" Physiol. Res. (2002) 51(1):85-91.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.
Smith et al., "Comparison of biosequences" Adv. Appl. Math. (1981) 2(4):482-489.
Sofia et al., "Discovery of a beta-d-2'-deoxy-2'-alpha-fluoro-2'-beta-C-methyluridine Nucleotide Prodrug (PSA-7977) For the Treatment of Hepatitis C virus" J. Med. Chem. (2010) 53(19): 7202-7218.
Solfrizzi et al., "Lipoprotein(a), apolipoprotein E genotype, and risk of Alzheimer's disease" J Neurol Neurosurg Psychiatry (2002) 72(6): 732-736.
Sonnenburg et al., "GPIHBP1 stabilizes lipoprotein lipase and prevents its inhibition by angiopoietin-like 3 and angiopoietin-like 4" The Journal of Lipid Research (2009) 50(12): 2421-2429.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tober et al., "Self-Metathesis of Polyol Allyl Ethers towards Carbohydrate-Based Oligohydroxy Derivatives" Eur. J. Org. Chem. (2013) 3: 566-577.
Tomiya et al., "Liver-targeting of primaquine-(poly-c-glutamic acid) and its degradation in rat hepatocytes" Bioorganic & Medicinal Chemistry (2013) 21: 5275-5281.
Toyokuni et al., "Synthetic vaccines: I. Synthesis of multivalent Tn antigen cluster-lysyllysine conjugates" Tetrahedron Lett (1990) 31(19): 2673-2676.
Tsimikas et al., "Relationship of oxidized phospholipids on apolipoprotein B-100 particles to race/ethnicity, apolipoprotein(a) isoform size, and cardiovascular risk factors: results from the Dallas Heart Study" Circulation (2009) 119(13): 1711-1719.
Tsimikas et al., "Antisense therapy targeting apolipoprotein(a): a randomised, double-blind, placebo-controlled phase 1 study" Lancet (2015) 386: 1472-1483.
Valdivielso et al., "Association of moderate and severe hypertriglyceridemia with obesity, diabetes mellitus and vascular disease in the Spanish working population: results of the ICARIA study" Atherosclerosis (2009) 207(2):573-578.
Valentijn et al., "Solid-phase Synthesis of Lysine-based Cluster Galactosides with High Affinity for the Asialoglycoprotein Receptor" Tetrahedron (1997) 53(2): 759-770.
Van Rossenberg et al., "Stable polyplexes based on arginine-containing oligopeptides for in vivo gene delivery" Gene Ther (2004) 11: 457-464.
Verbeure et al., "RNase H mediated cleavage of RNA by cyclohexene nucleic acid (CeNA)" Nucleic Acids Res. (2001) 29(24):4941-4947.
Verdel et al., "RNAi-mediated targeting of heterochromatin by the RITS complex" Science (2004) 303(5668):672-676.
Viney et al., "Relationship between "LDL-C", estimated true LDL-C, apolipoprotein B-100, and PCSK9 levels following lipoprotein(a) lowering with an antisense oligonucleotide" J Clin Lipidology (2018) 12: 702-710.
Viney et al., "Antisense oligonucleotides targeting apolipoprotein(a) in people with raised lipoprotein(a): two randomised, double-blind, placebo-controlled, dose-ranging trials" Lancet (2016) 388: 2239-2253.
Volpe et al., "Regulation of heterochromatic silencing and histone H3 lysine-9 methylation by RNAi" Science (2002) 297(5588):1833:1837.
Wahlestedt et al., "Potent and nontoxic antisense oligonucleotide containing locked nucleic acids" Proc. Natl. Acad. Sci. USA (2000) 97: 5633-5638.
Wang et al., "A straightforward stereoselective synthesis of D- and L-5-hydroxy-4-hydroxymethyl-2-cyclohexenylguanine" J. Org. Chem. (2001) 66(25):8478-8482.

(56) References Cited

OTHER PUBLICATIONS

Wang et al., "Cyclohexene nucleic acids (CeNA) form stable duplexes with RNA and induce RNase H activity" Nucleosides Nucleotides Nucleic Acids (2001) 20(4-7):785-788.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.

Wang et al., "Stereocontrolled synthesis of ara-type cyclohexenyl nucleosides" J. Org. Chem. (2003) 68(11):4499-4505.

Weber et al., "Design and synthesis of P2-P1'-linked macrocyclic human renin inhibitors" J. Med. Chem. (1991) 34(9): 2692-2701.

Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.

Willer et al., "Newly identified loci that influence lipid concentrations and risk of coronary artery disease" Nat. Genet. (2008) 40(2):161-169.

Woolf et al. "Specificity of antisense oligonucleotides in vivo" PNAS (1992) 89:7305-7309.

Wu et al., "A New N-Acetylgalactosamine Containing Peptide as a Targeting Vehicle for Mammalian Hepatocytes Via Asialoglycoprotein Receptor Endocytosis" Current Drug Delivery (2004) 1: 119-127.

Yu et al., "Effects of ANGPTL3 antisense oligodeoxynucleotides transfection on the cell growths and invasion of human hepatocellular carcinoma cells" Hepatogastroenterology (2011) 58(110-111):1742-6.

Yuan et al., "Hypertriglyceridemia: its etiology, effects and treatment" CMAJ (2007) 176(8): 1113-1120.

Zhang et al., "PowerBLAST: A New Network Blast Application for Interactive or Automated Sequence Analysis and Annotation" Genome Res. (1997) 7:649-656.

Zhang et al., "Spontaneous atherosclerosis in aged lipoprotein lipase-deficient mice with severe hypertriglyceridemia on a normal chow diet" Circ. Res. (2008) 102(2):250-256.

Zhao et al., "Synthesis and preliminary biochemical studies with 5'-deoxy-5'-methylidyne phosphonate linked thymidine oligonucleotides" Tetrahedron Letters (1996) 37(35): 6239-6242.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Zhou et al., "Proteolytic processing in the secretory pathway." J. Biol. Chem. (1999) 274(30): 20745-20748.

International Search Report for application PCT/US11/20606 dated Jun. 27, 2011.

International Search Report for Application PCT/US12/52884 dated Nov. 20, 2012.

International Search Report for Application PCT/US14/36460 dated Oct. 10, 2014.

International Search Report for Application PCT/US14/36466 dated Dec. 1, 2014.

International Search Report for Application PCT/US14/36462 dated Dec. 23, 2014.

International Search Report for Application PCT/US14/56630 dated Dec. 24, 2014.

International Search Report for Application PCT/US14/43731 dated Dec. 10, 2014.

International Search Report for Application PCT/US14/36463 dated Dec. 30, 2014.

International Search Report for PCT/US16/060831 dated Jan. 31, 2017.

International Search Report for Application PCT/US16/60816 dated Feb. 3, 2017.

\* cited by examiner

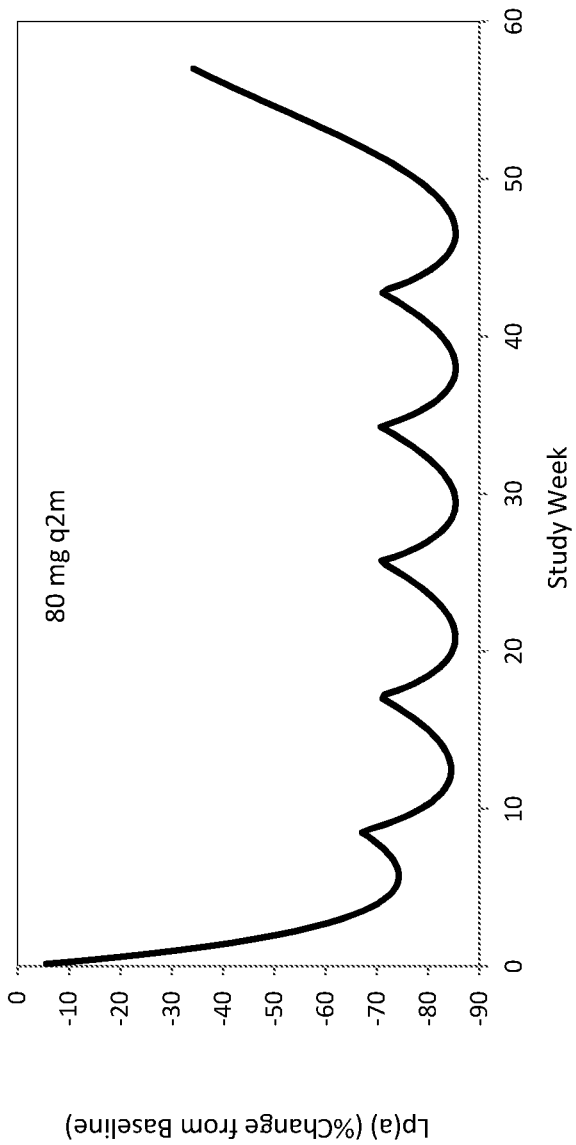

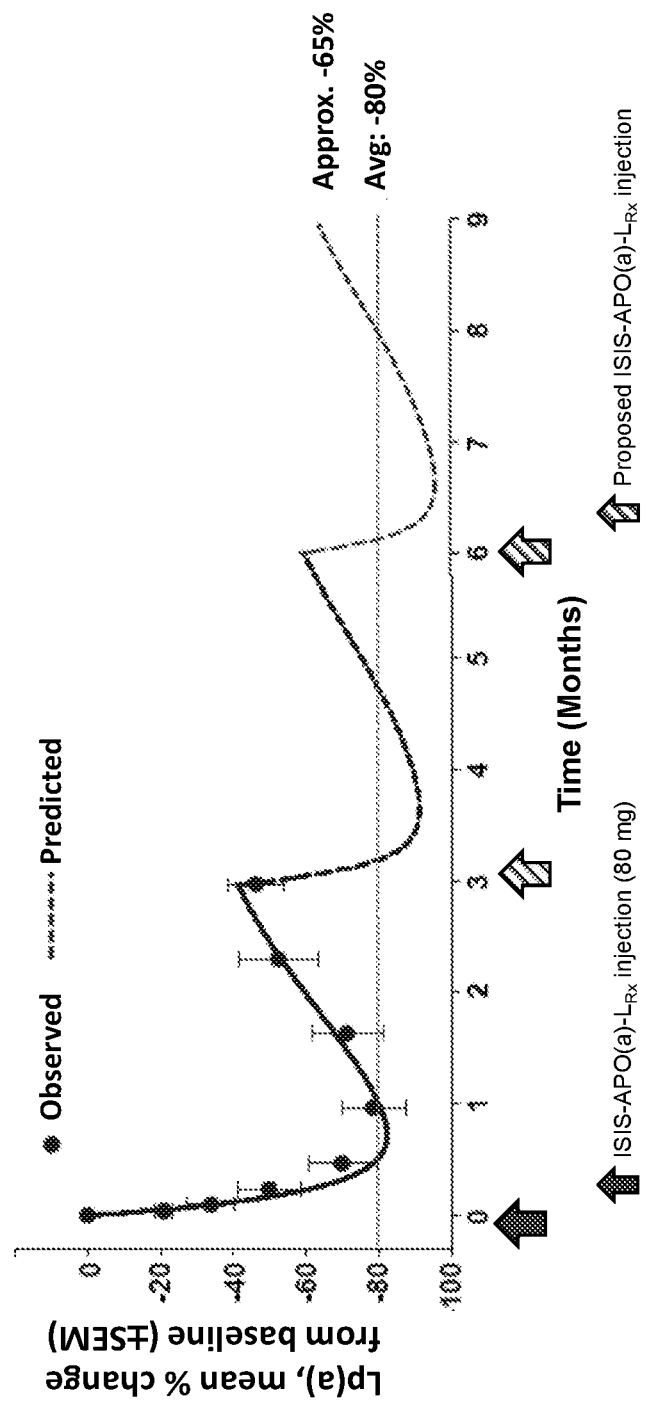

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tgctccgttg gtgcttgttc                                              20
```

MODULATING APOLIPOPROTEIN (A) EXPRESSION

SEQUENCE LISTING

The present application is being filed along with a Sequence Listing in electronic format. The Sequence Listing is provided as a file, created on Apr. 30, 2018, which is 4 Kb in size. The information in the electronic format of the sequence listing is incorporated herein by reference in its entirety.

BACKGROUND OF THE INVENTION

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced siliencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of diseases.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

The lipoprotein(a) [Lp(a)] particle was identified nearly 50 years ago and is comprised of a highly unique LDL particle in which one apolipoprotein B (apoB) protein is linked via a disulfide bond to a single apolipoprotein(a)

[apo(a)] protein. The apo(a) protein shares a high degree of homology with plasminogen particularly within the kringle IV type 2 repetitive domain. Levels of circulating Lp(a) are inversely proportional to the number of kringle IV type 2 variable repeats present in the molecule and, as both alleles are co-expressed within individuals, can display heterozygous plasma isoform profiles (Kraft et al., Eur J Hum Genet, 1996; 4(2): 74-87). It is thought that this kringle repeat domain in apo(a) may be responsible for its pro-thrombotic and anti-fibrinolytic properties, potentially enhancing atherosclerotic progression.

Apo(a) is transcriptionally regulated by IL-6 and in studies in rheumatoid arthritis patients treated with an IL-6 inhibitor (tocilizumab), plasma levels were reduced by 30% after 3 month treatment (Schultz et al., PLoS One 2010; 5:e14328).

Apo(a) has been shown to preferentially bind oxidized phospholipids and potentiate vascular inflammation (Bergmark et al., J Lipid Res 2008; 49:2230-2239; Tsimikas et al., Circulation. 2009; 119(13):1711-1719).

Further, studies suggest that the Lp(a) particle may also stimulate endothelial permeability, induce plasminogen activator inhibitor type-1 expression and activate macrophage interleukin-8 secretion (Koschinsky and Marcovina, Curr Opin Lipidol 2004; 15:167-174). Importantly, recent genetic association studies revealed that Lp(a) was an independent risk factor for myocardial infarction, stroke, peripheral vascular disease and abdominal aortic aneurysm (Rifai et al., Clin Chem 2004; 50:1364-71; Erqou et al., JAMA 2009; 302:412-23; Kamstrup et al., Circulation 2008; 117:176-84). Further, in the recent Precocious Coronary Artery Disease (PROCARDIS) study, Clarke et al. (Clarke et al., NEJM (2009) 361; 2518-2528) described robust and independent associations between coronary heart disease and plasma Lp(a) concentrations. Additionally, Solfrizzi et al., suggested that increased serum Lp(a) may be linked to an increased risk for Alzheimer's Disease (AD) (Solfrizzi et al., J Neurol Neurosurg Psychiatry 2002, 72:732-736. Currently, in the clinic setting, examples of indirect apo(a) inhibitors for treating cardiovascular disease include aspirin, Niaspan, Mipomersen, Anacetrapib, Epirotirome and Lomitapide which reduce plasma Lp(a) levels by 18%, 39%, 32%, 36%, 43% and 17%, respectively. Additionally, Lp(a) apheresis has been used in the clinic to reduce apo(a) containing Lp(a) particles.

To date, therapeutic strategies to treat cardiovascular disease by directly targeting apo(a) levels have been limited. Ribozyme oligonucleotides (U.S. Pat. No. 5,877,022) and antisense oligonucleotides (WO 2005/000201; WO 2003/014397; WO2013/177468; US20040242516; U.S. Pat. Nos. 8,138,328, 8,673,632 and 7,259,150; Merki et al., J Am Coll Cardiol 2011; 57:1611-1621; each publication incorporated by reference in its entiretly) have been developed but none have been approved for commercial use.

WO 2014/179625 discloses antisense compounds targeting apo(a), including ISIS 681257.

Tsimikas et al. (Lancet. 2015 Oct. 10; 386:1472-83) discloses the results of a randomized, double-blind, placebo-controlled Phase 1 study using an antisense compound targeting human apo(a): ISIS 494372 (also known as ISIS-APO(a)Rx).

One chemical modification used to improve the activity of RNAse H dependent (gapmer) antisense compounds, including Apo(a) targeting compounds, in vivo is conjugation to a conjugate group, such as a GalNAc cluster. Conjugation to a conjugate group has been shown to improve potency in vivo in non-human subjects, for example including the use of RNAse H dependent (gapmer) antisense compounds conjugated to GalNAc clusters as disclosed in WO 2014/179620. Prior to the present invention, no RNAse H dependent (gapmer) antisense compounds conjugated to GalNAc clusters had been tested in humans to achieve target reduction.

There remains an unmet medical need for novel agents which can potently and selectively reduce apo(a) levels in humans, including in patients at enhanced risk for cardiovascular events due to chronically elevated plasma Lp(a) levels.

SUMMARY OF THE INVENTION

The present disclosure provides methods of treating a disease or condition in a human by administering ISIS 681257 to a human, especially a human at enhanced risk for cardiovascular events due to chronically elevated plasma Lp(a) levels. ISIS 681257 has the following structure, which includes salts thereof:

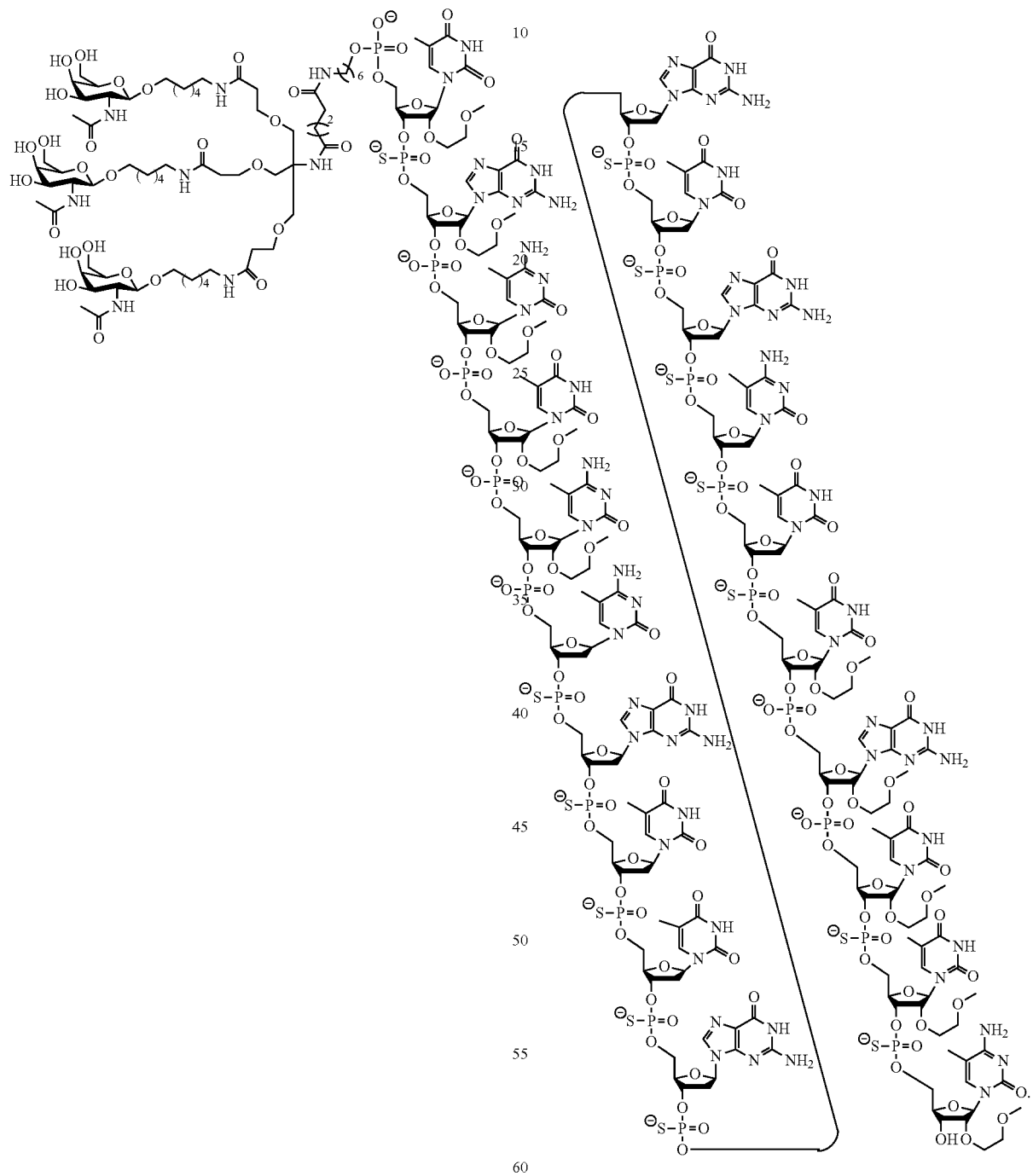

Pictured below is an example of a salt of ISIS 681257:

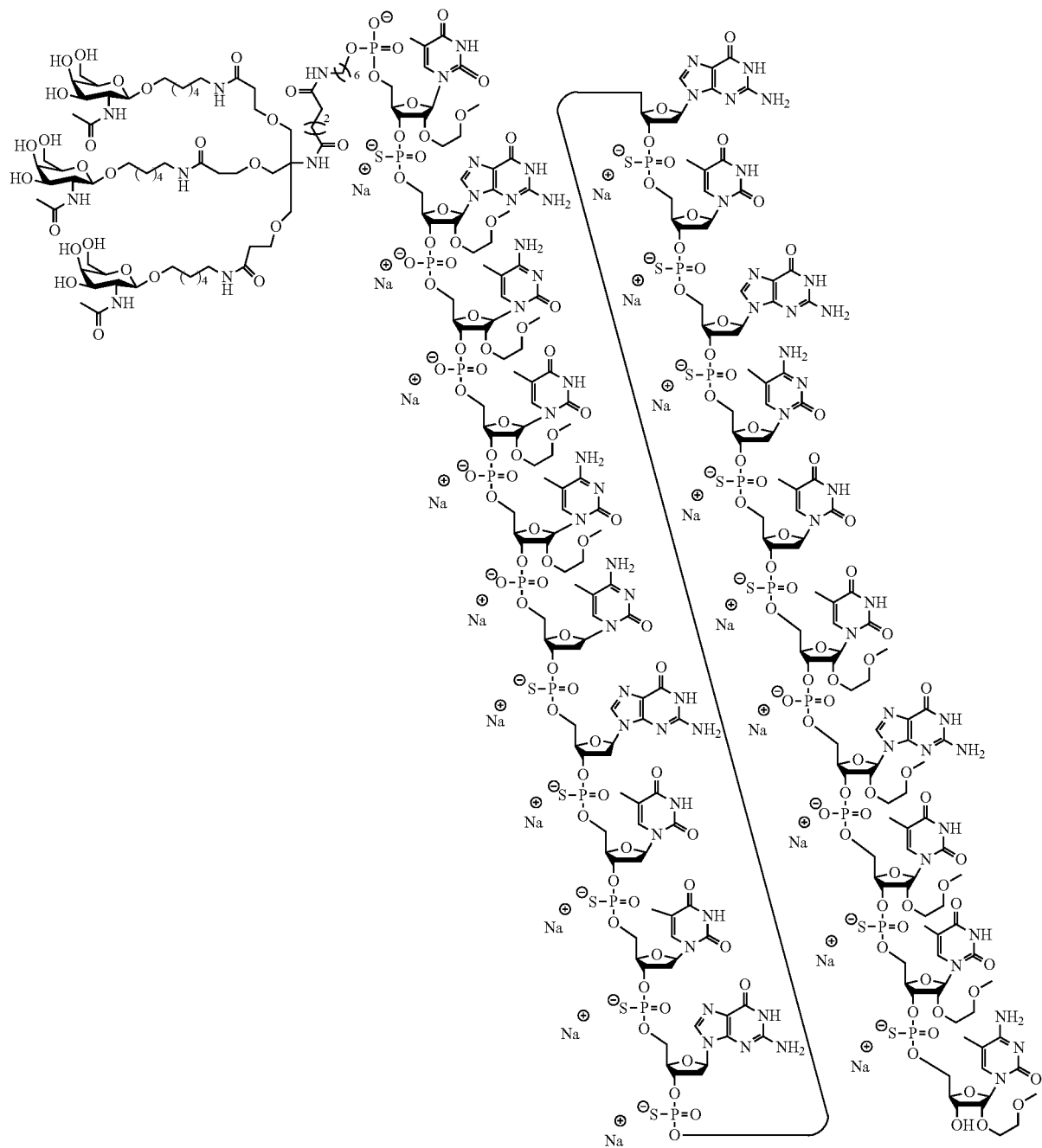

ISIS 681257 comprises a modified oligonucleotide having the nucleobase sequence TGCTCCGTTGGTGCTTGTTC (SEQ ID NO.: 1), a 5-10-5 gapmer motif, and a GalNAc conjugate. As illustrated in the present disclosure, ISIS 681257 represents a major advance in treating humans. When administered to humans, ISIS 681257 is particularly efficacious at lowering Apo(a) mRNA and plasma Lp(a), in terms of both its potency and its duration of action. As illustrated by the data provided herein, ISIS 681257 has ≥30-fold increase in humans compared to a modified oligonucleotide having the same nucleobase sequence and the same 5-10-5 gapmer motif, but lacking a GalNAc conjugate. ISIS 681257 provides excellent reduction of Apo(a) mRNA and plasma Lp(a) and enables efficacious dosing of once a week, once a month, once every two months, or once every three months.

The clinical results presented herein for ISIS 681257 are surprising, because earlier experiments involving both the unconjugated compound (ISIS 494372 also having the nucleobase sequence TGCTCCGTTGGTGCTTGTTC (SEQ ID NO.: 1) and a 5-10-5 gapmer motif, and the GalNAc conjugated compound (ISIS 681257) had suggested that the GalNAc conjugated compound would have significantly lower potency and/or a shorter duration of action in humans than was observed following the first dosing of humans reported herein (e.g. see Examples 89, 100 and 108 of WO 2014/179625 and Tsimikas et al., Lancet, 2015 Oct. 10; 386:1472-83). Earlier experiments involving both ISIS 494372 and ISIS 681257 had indicated that the GalNAc conjugated compound benefits from higher in vivo potency in mice, but these earlier experiments did not reveal or predict the unexpected ≥30-fold improvement in humans. In earlier experiments ISIS 681257 was found to have around 13-fold improved potency (on baseline plasma Lp(a) levels) relative to ISIS 494372 in human transgenic Apo(a) mice (ISIS 681257 ED50=0.8 mg/kg/wk; ISIS 494372 ED50=11 mg/kg/wk). The fold improvement in potency between ISIS 494372 and ISIS 681257 observed in the human Phase 1 clinical trials was surprisingly over 2 times higher than the fold improvement observed for the same pair of compounds in mice, and this was unexpected. In light of these surprising results, when treating humans, the GalNAc conjugated compound (ISIS 681257 and its salts) can be administered at lower doses and/or less frequently than expected based on the earlier in vivo testing of the GalNAc conjugated compound. See, e.g., Viney, et al. Lancet, 2016, September 2016; 388: 2239-53. This can provide one or more very significant improvements in treating humans, e.g. reduced cost of treatment, improved patient compliance, reduced volume of administered medicinal product and/or potentially reduced risk of potential adverse events via lower dose administration regimens.

The present disclosure provides the following non-limiting embodiments:

Embodiment 1

An oligomeric compound, wherein the oligomeric compound is ISIS 681257, for use in treating or preventing a disease or condition in a human, wherein the treatment comprises administering not more than 500 mg of the oligomeric compound to the human during a dosing period.

Embodiment 2

The oligomeric compound for use according to embodiment 1, wherein the treatment comprises administering not more than 250 mg of the oligomeric compound to the human during the dosing period.

Embodiment 3

The oligomeric compound for use according to embodiment 1, wherein the treatment comprises administering not more than 100 mg of the oligomeric compound to the human during the dosing period.

Embodiment 4

The oligomeric compound for use according to embodiment 1, wherein the treatment comprises administering not more than 50 mg of the oligomeric compound to the human during the dosing period.

Embodiment 5

The oligomeric compound for use according to embodiment 1, wherein the treatment comprises administering not more than 25 mg of the oligomeric compound to the human during the dosing period.

Embodiment 6

The oligomeric compound for use according to embodiment 1, wherein the treatment comprises administering not more than 15 mg of the oligomeric compound to the human during the dosing period.

Embodiment 7

The oligomeric compound for use according to any of embodiments 1-6, wherein the dosing period is three months.

Embodiment 8

The oligomeric compound for use according to any of embodiments 1-6, wherein the dosing period is two months.

Embodiment 9

The oligomeric compound for use according to any of embodiments 1-6, wherein the dosing period is one month.

Embodiment 10

The oligomeric compound for use according to any of embodiments 1-6, wherein the dosing period is four weeks.

Embodiment 11

The oligomeric compound for use according to any of embodiments 1-6, wherein the dosing period is three weeks.

Embodiment 12

The oligomeric compound for use according to any of embodiments 1-6, wherein the dosing period is two weeks.

Embodiment 13

The oligomeric compound for use according to any of embodiments 1-6, wherein the dosing period is one week.

Embodiment 14

The oligomeric compound for use according to any preceding embodiment, wherein the treatment comprises administering a unit dose comprising not more than 125 mg of the oligomeric compound.

Embodiment 15

The oligomeric compound for use according to any preceding embodiment, wherein the treatment comprises administering a unit dose comprising not more than 100 mg of the oligomeric compound.

Embodiment 16

The oligomeric compound for use according to any preceding embodiment, wherein the treatment comprises administering a unit dose comprising not more than 75 mg of the oligomeric compound.

Embodiment 17

The oligomeric compound for use according to any preceding embodiment, wherein the treatment comprises administering a unit dose comprising not more than 50 mg of the oligomeric compound.

Embodiment 18

The oligomeric compound for use according to any preceding embodiment, wherein the treatment comprises administering a unit dose comprising not more than 25 mg of the oligomeric compound.

Embodiment 19

The oligomeric compound for use according to any preceding embodiment, wherein the treatment comprises administering a unit dose comprising not more than 15 mg of the oligomeric compound.

Embodiment 20

The oligomeric compound for use according to any of embodiments 14-19, wherein the treatment comprises administering a unit dose comprising not less than 1 mg of the oligomeric compound.

Embodiment 21

The oligomeric compound for use according to embodiment 20, wherein the treatment comprises administering a unit dose comprising not less than 2.5 mg of the oligomeric compound

Embodiment 22

The oligomeric compound for use according to embodiment 20, wherein the treatment comprises administering a unit dose comprising not less than 5 mg of the oligomeric compound

Embodiment 23

The oligomeric compound for use according to any of embodiments 14-22, wherein the treatment comprises administering a unit dose of from 75 mg to 85 mg, and optionally a unit dose of 80 mg.

Embodiment 24

The oligomeric compound for use according to any of embodiments 14-22, wherein the treatment comprises administering a unit dose of from 55 mg to 65 mg, and optionally a unit dose of 60 mg.

Embodiment 25

The oligomeric compound for use according to any of embodiments 14-22, wherein the treatment comprises administering a unit dose of from 35 mg to 45 mg, and optionally a unit dose of 40 mg.

Embodiment 26

The oligomeric compound for use according to any of embodiments 14-22, wherein the treatment comprises administering a unit dose of from 25 mg to 35 mg, and optionally a unit dose of 30 mg.

Embodiment 27

The oligomeric compound for use according to any of embodiments 14-22, wherein the treatment comprises administering a unit dose of from 15 mg to 25 mg, and optionally a unit dose of 20 mg.

Embodiment 28

The oligomeric compound for use according to any of embodiments 14-22, wherein the treatment comprises administering a unit dose of from 5 mg to 15 mg, and optionally a unit dose of 10 mg.

Embodiment 29

The oligomeric compound for use according to any of embodiments 14-28, wherein the treatment comprises administering not more than 1 unit dose to the human during the dosing period.

Embodiment 30

The oligomeric compound for use according to any of embodiments 14-28, wherein the treatment comprises administering not more than 2 unit doses to the human during the dosing period.

Embodiment 31

The oligomeric compound for use according to any of embodiments 14-28, wherein the treatment comprises administering not more than 3 unit doses to the human during the dosing period.

Embodiment 32

The oligomeric compound for use according to any of embodiments 14-28, wherein the treatment comprises administering not more than 4 unit doses to the human during the dosing period.

Embodiment 33

The oligomeric compound for use according to any of embodiments 14-28, wherein the treatment comprises administering not more than 5 unit doses to the human during the dosing period.

Embodiment 34

The oligomeric compound for use according to any of embodiments 14-28, wherein the treatment comprises administering not more than 6 unit doses to the human during the dosing period.

Embodiment 35

The oligomeric compound for use according to any of embodiments 1-34, wherein:
(i) the treatment comprises administering not more than 100 mg of the oligomeric compound to the human during the dosing period; and (ii) the dosing period is three months.

Embodiment 36

The oligomeric compound for use according to embodiment 35, wherein (i) the treatment comprises administering not more than 100 mg of the oligomeric compound to the human during the dosing period; (ii) the dosing period is three months; and (iii) the treatment comprises administering not more than one unit dose to the human during the dosing period.

Embodiment 37

The oligomeric compound according to embodiment 35 or embodiment 36, wherein the treatment comprises administering from 75 mg to 85 mg, optionally 80 mg, of the oligomeric compound to the human during the dosing period.

Embodiment 38

The oligomeric compound for use according to any of embodiments 1-34, wherein:
(i) the treatment comprises administering not more than 100 mg of the oligomeric compound to the human during the dosing period; and (ii) the dosing period is two months.

Embodiment 39

The oligomeric compound for use according to embodiment 38, wherein (i) the treatment comprises administering not more than 100 mg of the oligomeric compound to the human during the dosing period; (ii) the dosing period is two months; and (iii) the treatment comprises administering not more than one unit dose to the human during the dosing period.

Embodiment 40

The oligomeric compound according to embodiment 38 or embodiment 39, wherein the treatment comprises administering from 75 mg to 85 mg, optionally 80 mg, of the oligomeric compound to the human during the dosing period.

Embodiment 41

The oligomeric compound for use according to any of embodiments 1-34, wherein:
(i) the treatment comprises administering not more than 100 mg of the oligomeric compound to the human during the dosing period; and (ii) the dosing period is one month.

Embodiment 42

The oligomeric compound for use according to embodiment 41, wherein (i) the treatment comprises administering not more than 100 mg of the oligomeric compound to the human during the dosing period; (ii) the dosing period is one month; and (iii) the treatment comprises administering not more than one unit dose to the human during the dosing period.

Embodiment 43

The oligomeric compound according to embodiment 41 or embodiment 42, wherein the treatment comprises administering from 75 mg to 85 mg, optionally 80 mg, of the oligomeric compound to the human during the dosing period.

Embodiment 44

The oligomeric compound for use according to any of embodiments 1-34, wherein:
(i) the treatment comprises administering not more than 75 mg of the oligomeric compound to the human during the dosing period; and (ii) the dosing period is one month.

Embodiment 45

The oligomeric compound for use according to embodiment 44, wherein (i) the treatment comprises administering not more than 75 mg of the oligomeric compound to the human during the dosing period; (ii) the dosing period is one month; and (iii) the treatment comprises administering not more than one unit dose to the human during the dosing period.

Embodiment 46

The oligomeric compound according to embodiment 44 or embodiment 45, wherein the treatment comprises administering from 55 mg to 65 mg, optionally 60 mg, of the oligomeric compound to the human during the dosing period.

Embodiment 47

The oligomeric compound for use according to any of embodiments 1-34, wherein:
(i) the treatment comprises administering not more than 50 mg of the oligomeric compound to the human during the dosing period; and (ii) the dosing period is one week.

Embodiment 48

The oligomeric compound for use according to embodiment 47, wherein (i) the treatment comprises administering not more than 50 mg of the oligomeric compound to the human during the dosing period; (ii) the dosing period is one week; and (iii) the treatment comprises administering not more than one unit dose to the human during the dosing period.

Embodiment 49

The oligomeric compound according to embodiment 47 or embodiment 48, wherein the treatment comprises administering from 35 mg to 45 mg, optionally 40 mg, of the oligomeric compound to the human during the dosing period.

Embodiment 50

The oligomeric compound according to embodiment 47 or embodiment 48, wherein the treatment comprises administering from 25 mg to 35 mg, optionally 30 mg, of the oligomeric compound to the human during the dosing period.

Embodiment 51

The oligomeric compound according to embodiment 47 or embodiment 48, wherein the treatment comprises administering from 15 mg to 25 mg, optionally 20 mg, of the oligomeric compound to the human during the dosing period.

Embodiment 52

The oligomeric compound according to embodiment 47 or embodiment 48, wherein the treatment comprises administering from 5 mg to 15 mg, optionally 10 mg, of the oligomeric compound to the human during the dosing period.

Embodiment 53

The oligomeric compound for use according to any of embodiments 1-34, wherein: (i) the treatment comprises administering not more than 250 mg of the oligomeric compound to the human during the dosing period; and (ii) the dosing period is four weeks.

Embodiment 54

The oligomeric compound for use according to embodiment 53, wherein the treatment comprises administering 40 mg of the oligomeric compound six times during the dosing period.

Embodiment 55

The oligomeric compound for use according to embodiment 53 or embodiment 54, wherein (i) the treatment comprises administering 40 mg of the oligomeric compound six times during the dosing period, and (ii) once per week thereafter.

Embodiment 56

The oligomeric compound for use according to embodiment 53, wherein the treatment comprises administering 30 mg of the oligomeric compound six times during the dosing period.

Embodiment 57

The oligomeric compound for use according to embodiment 53 or embodiment 56, wherein (i) the treatment comprises administering 30 mg of the oligomeric compound six times during the dosing period, and (ii) once per week thereafter.

Embodiment 58

The oligomeric compound for use according to embodiment 53, wherein the treatment comprises administering 20 mg of the oligomeric compound six times during the dosing period.

Embodiment 59

The oligomeric compound for use according to embodiment 53 or embodiment 58, wherein (i) the treatment comprises administering 20 mg of the oligomeric compound six times during the dosing period, and (ii) once per week thereafter.

Embodiment 60

The oligomeric compound for use according to any of embodiments 1-59, wherein the human is at enhanced risk for cardiovascular events due to elevated plasma Lp(a) levels.

Embodiment 61

The oligomeric compound for use according to any of embodiments 1-59, wherein the disease or condition is selected from calcific aortic valve stenosis with elevated Lp(a), elevated cardiovascular risk with elevated Lp(a), and recurrent cardiovascular events with elevated Lp(a).

Embodiment 62

The oligomeric compound for use according to any preceding embodiment, wherein the oligomeric compound is administered to the human by injection.

Embodiment 63

The oligomeric compound for use according to embodiment 62, wherein the oligomeric compound is administered to the human by subcutaneous injection.

Embodiment 64

The oligomeric compound for use according to embodiment 62 or embodiment 63, wherein the oligomeric compound is formulated in a sterile liquid and optionally wherein each unit dose of the oligomeric compound is not more than 1 mL of the sterile liquid.

Embodiment 65

The oligomeric compound for use according to embodiment 64, wherein each unit dose of the oligomeric compound is not more than 0.8 mL of the sterile liquid.

Embodiment 66

The oligomeric compound for use according to embodiment 64, wherein each unit dose of the oligomeric compound is not more than 0.5 mL of the sterile liquid.

Embodiment 67

The oligomeric compound for use according to embodiment 64, wherein each unit dose of the oligomeric compound is not more than 0.4 mL of the sterile liquid.

Embodiment 68

The oligomeric compound for use according to embodiment 64, wherein each unit dose of the oligomeric compound is not more than 0.25 mL of the sterile liquid.

Embodiment 69

The oligomeric compound for use according to embodiment 64, wherein each unit dose of the oligomeric compound is not more than 0.2 mL of the sterile liquid.

Embodiment 70

The oligomeric compound for use according to any of embodiments 64 to 69, wherein the sterile liquid is water.

Embodiment 71

The oligomeric compound for use according to any of embodiments 64 to 69, wherein the sterile liquid is water with a sodium phosphate buffer.

Embodiment 72

The oligomeric compound for use according to any of embodiments 64 to 69, wherein the sterile liquid is water with a sodium phosphate buffer and sodium chloride.

Embodiment 73

The oligomeric compound for use according to any preceding embodiment, wherein the treatment reduces the fasting plasma Lp(a) concentration in the human by at least 50%, when the fasting plasma Lp(a) concentration in the human is measured at the start and end of the dosing period.

Embodiment 74

The oligomeric compound for use according to any preceding embodiment, wherein the treatment reduces the fasting plasma Lp(a) concentration in the human by at least 75%, when the fasting plasma Lp(a) concentration in the human is measured at the start and end of the dosing period

Embodiment 75

The oligomeric compound for use according to any preceding embodiment, wherein the treatment reduces the fasting plasma Lp(a) concentration in the human by at least 80%, when the fasting plasma Lp(a) concentration in the human is measured at the start and end of the dosing period.

Embodiment 76

The oligomeric compound for use according to any preceding embodiment, wherein the treatment reduces the fasting plasma Lp(a) concentration in the human by at least 85%, when the fasting plasma Lp(a) concentration in the human is measured at the start and end of the dosing period.

Embodiment 77

A pharmaceutical composition comprising an oligomeric compound and one or more pharmaceutically acceptable carriers or diluents, wherein the oligomeric compound is ISIS 681257, and wherein the pharmaceutical composition contains not more than 125 mg of the oligomeric compound.

Embodiment 78

The pharmaceutical composition of embodiment 77, wherein the pharmaceutical composition contains not more than 100 mg of the oligomeric compound.

Embodiment 79

The pharmaceutical composition of embodiment 77, wherein the pharmaceutical composition contains not more than 75 mg of the oligomeric compound.

Embodiment 80

The pharmaceutical composition of embodiment 77, wherein the pharmaceutical composition contains not more than 50 mg of the oligomeric compound.

Embodiment 81

The pharmaceutical composition of embodiment 77, wherein the pharmaceutical composition contains not more than 25 mg of the oligomeric compound.

Embodiment 82

The pharmaceutical composition of embodiment 77, wherein the pharmaceutical composition contains not more than 15 mg of the oligomeric compound.

Embodiment 83

The pharmaceutical composition of embodiment 77, wherein the pharmaceutical composition contains not more than 10 mg of the oligomeric compound.

Embodiment 84

The pharmaceutical composition of embodiment 77, wherein the pharmaceutical composition contains not less than 1 mg of the oligomeric compound.

Embodiment 85

The pharmaceutical composition of embodiment 77, wherein the pharmaceutical composition contains not less than 2.5 mg of the oligomeric compound.

Embodiment 86

The pharmaceutical composition of embodiment 77, wherein the pharmaceutical composition contains not less than 5 mg of the oligomeric compound.

Embodiment 87

The pharmaceutical composition of embodiment 77, wherein the pharmaceutical composition contains not less than 10 mg of the oligomeric compound.

Embodiment 88

The pharmaceutical composition according to embodiment 77, wherein the composition comprises from 75 mg to 85 mg, and optionally 80 mg, of the oligomeric compound.

Embodiment 89

The pharmaceutical composition according to embodiment 77, wherein the composition comprises from 55 mg to 65 mg, and optionally 60 mg, of the oligomeric compound.

Embodiment 90

The pharmaceutical composition according to embodiment 77, wherein the composition comprises from 35 mg to 45 mg, and optionally 40 mg, of the oligomeric compound.

Embodiment 91

The pharmaceutical composition according to embodiment 77, wherein the composition comprises from 25 mg to 35 mg, and optionally 30 mg, of the oligomeric compound.

Embodiment 92

The pharmaceutical composition according to embodiment 77, wherein the composition comprises from 15 mg to 25 mg, and optionally 20 mg, of the oligomeric compound.

Embodiment 93

The pharmaceutical composition according to embodiment 77, wherein the composition comprises from 5 mg to 15 mg, and optionally 10 mg, of the oligomeric compound.

Embodiment 94

The pharmaceutical composition according to any of embodiments 77-93, wherein the composition is formulated for administration to a human by injection.

Embodiment 95

The pharmaceutical composition according to embodiment 94, wherein the oligomeric compound is formulated in a sterile liquid and optionally the composition is not more than 1 mL of the sterile liquid.

Embodiment 96

The pharmaceutical composition according to embodiment 95, wherein the pharmaceutical composition is not more than 0.8 mL of the sterile liquid.

Embodiment 97

The pharmaceutical composition according to embodiment 95, wherein the pharmaceutical composition is not more than 0.5 mL of the sterile liquid.

Embodiment 98

The pharmaceutical composition according to embodiment 95, wherein the pharmaceutical composition is not more than 0.4 mL of the sterile liquid.

Embodiment 99

The pharmaceutical composition according to embodiment 95, wherein the pharmaceutical composition is not more than 0.25 mL of the sterile liquid.

Embodiment 100

The pharmaceutical composition according to embodiment 95, wherein the pharmaceutical composition is not more than 0.2 mL of the sterile liquid.

Embodiment 101

The pharmaceutical composition according to any of embodiments 95 to 100, wherein the sterile liquid is water.

Embodiment 102

The pharmaceutical composition according to any of embodiments 95 to 100, wherein the sterile liquid is water with a sodium phosphate buffer.

Embodiment 103

The pharmaceutical composition according to any of embodiments 95 to 100, wherein the sterile liquid is water with a sodium phosphate buffer and sodium chloride.

Embodiment 104

The pharmaceutical composition according to any of embodiments 77-103, wherein administering the composition to a human reduces the fasting plasma Lp(a) concentration in the human by at least 50%, when the fasting plasma Lp(a) concentration in the human is measured at the start and end of the dosing period.

Embodiment 105

The pharmaceutical composition according to any of embodiments 77-103, wherein administering the composition to a human reduces the fasting plasma Lp(a) concentration in the human by at least 75%, when the fasting plasma Lp(a) concentration in the human is measured at the start and end of the dosing period

Embodiment 106

The pharmaceutical composition according to any of embodiments 77-103, wherein administering the composition to a human reduces the fasting plasma Lp(a) concentration in the human by at least 80%, when the fasting plasma Lp(a) concentration in the human is measured at the start and end of the dosing period.

Embodiment 107

The pharmaceutical composition according to any of embodiments 77-103, wherein administering the composition to a human reduces the fasting plasma Lp(a) concentration in the human by at least 85%, when the fasting plasma Lp(a) concentration in the human is measured at the start and end of the dosing period.

Embodiment 108

A method for producing the pharmaceutical composition according to any of embodiments 77-107, wherein the method comprises combining not more than 125 mg of the oligomeric compound with one or more pharmaceutically acceptable diluents, excipients or carriers.

Embodiment 109

A packaged pharmaceutical product comprising: (a) multiple unit dosage forms each comprising a pharmaceutical composition according to any of embodiments 77-107; and (b) printed instructions describing the administration of the unit dosage forms for a treatment as set forth in any of embodiments 1-76.

Embodiment 110

A sterile sealed container which contains a pharmaceutical composition according to any one of embodiments 77-107.

Embodiment 111

The sterile container according to embodiment 110, wherein the container is a vial.

Embodiment 112

The sterile container according to embodiment 110, wherein the container is a syringe.

Embodiment 113

A packaged pharmaceutical product comprising: (a) multiple unit dosage forms each comprising a sealed sterile container according to any of embodiments 110-112; and (b) printed instructions describing the administration of the unit dosage forms for a treatment as set forth in any of embodiments 1-76.

Embodiment 114

A method of treating a disease or condition in a human, comprising administering not more than 500 mg of an oligomeric compound to the human during a dosing period, wherein the oligomeric compound is ISIS 681257.

Embodiment 115

The method of embodiment 114, wherein the method comprises a treatment as set forth in any of embodiments 1-76.

Embodiment 116

Use of ISIS 681257 in the manufacture of a pharmaceutical composition according to any of embodiments 77-107, a packaged pharmaceutical composition according to embodiment 109 or 113, or a sterile sealed container according to any of embodiments 110-112.

Embodiment 117

A method comprising administering a unit dose of ISIS 681257 to a subject in need thereof.

Embodiment 118

The method of embodiment 117, wherein the unit dose is 120 mg.

Embodiment 119

The method of embodiment 117, wherein the unit dose is 100 mg.

Embodiment 120

The method of embodiment 117, wherein the unit dose is 80 mg.

Embodiment 121

The method of embodiment 117, wherein the unit dose is 60 mg.

Embodiment 122

The method of embodiment 117, wherein the unit dose is 40 mg.

Embodiment 123

The method of embodiment 117, wherein the unit dose is 30 mg.

Embodiment 124

The method of embodiment 117, wherein the unit dose is 20 mg.

Embodiment 125

The method of embodiment 117, wherein the unit dose is 15 mg.

Embodiment 126

The method of embodiment 117, wherein the unit dose is 10 mg.

Embodiment 127

The method of any of embodiments 117 to 126, wherein the unit dose is administered once every week.

Embodiment 128

The method of any of embodiments 117 to 126, wherein the unit dose is administered once every 2 weeks.

Embodiment 129

The method of any of embodiments 117 to 126, wherein the unit dose is administered once every 3 weeks.

Embodiment 130

The method of any of embodiments 117 to 126, wherein the unit dose is administered once every 4 weeks.

Embodiment 131

The method of any of embodiments 117 to 126, wherein the unit dose is administered once every month.

Embodiment 132

The method of any of embodiments 117 to 126, wherein the unit dose is administered once every 2 months.

Embodiment 133

The method of any of embodiments 117 to 126, wherein the unit dose is administered once every 3 months.

Embodiment 134

The method of any of embodiments 117 to 126, wherein the unit dose is administered on day 1, 3, 5, 8, 15, 22, and once per week thereafter.

Embodiment 135

The method of any of embodiments 117 to 134, wherein the subject has one or more symptoms of a cardiovascular disease or disorder.

Embodiment 136

The method of embodiment 135, wherein one or more symptoms of the cardiovascular disease or disorder are ameliorated.

In certain embodiments, the present disclosure provides an oligomeric compound, wherein the oligomeric compound is ISIS 681257, for use in treating or preventing a disease or condition associated with elevated Lp(a) in a human, wherein the treatment comprises administering one or more doses of the oligomeric compound to the human in (a) a loading or induction phase, and (b) a maintenance phase. In certain embodiments, a dose of the oligomeric compound is administered to the human during the maintenance phase once per week, once every two weeks, once per month, once every two months or once quarterly, for as long as needed, effective, and/or tolerated.

In some embodiments, the treatment comprises administering not more than not more than 450 mg, not more than 400 mg, not more than 350 mg, not more than 300 mg, not more then 250 mg, not more than 200 mg, not more than 150 mg, not more than 100 mg, not more than 75 mg, not more than 50 mg, not more than 40 mg, not more than 30 mg, not more than 25 mg, not more than 20 mg, or not more than 15 mg, of the oligomeric compound to the human during the dosing period.

The present disclosure provides methods comprising administering ISIS 681257 to a patient in need thereof. In certain embodiments, a patient in need thereof is a human with elevated Apo(a) levels, for example, a human having apo(a) levels≥30 mg/dL, ≥35 mg/dL, ≥40 mg/dL, ≥50 mg/dL, ≥60 mg/dL, ≥70 mg/dL, ≥80 mg/dL, ≥90 mg/dL, ≥100 mg/dL, ≥110 mg/dL, ≥120 mg/dL, ≥130 mg/dL, ≥140 mg/dL, ≥150 mg/dL, ≥160 mg/dL, ≥170 mg/dL, ≥175 mg/dL, ≥180 mg/dL, ≥190 mg/dL, ≥200 mg/dL. Lp(a) may also be expressed in nanomoles per liter. For example, a human subject having ≥75 nanomoles/liter (nmol/L) or ≥30 mg/dL, would be considered at risk of one or more symptoms of a cardiovascular disease or disorder.

BRIEF DESCRIPTION OF THE FIGURES

FIG. 3 illustrates the predicted Lp (a) levels as a result of a 2-month dosing regimen (e.g. one dose every two months). An 80 mg dose every 2-months shows a steady state reduction of Lp (a) of about 80%.

FIG. 4 illustrates the predicted Lp (a) levels as a result of a quarterly dosing regimen. An 80 mg dose every quarter shows a steady state reduction of Lp (a) of 80% and maximum reduction of Lp (a) of >90%.

FIGS. 6A-D show modeling of the effect on Lp(a) by weekly administration of ISIS 681257 at doses of 5 mg (FIG. 6A), 10 mg (FIG. 6B), 20 mg (FIG. 6C), and 30 mg (FIG. 6D). The dark middle line represents the predicted dose, while the uppermost and lowermost lines represent the 90% Confidence Interval.

DETAILED DESCRIPTION

Figure 1A:
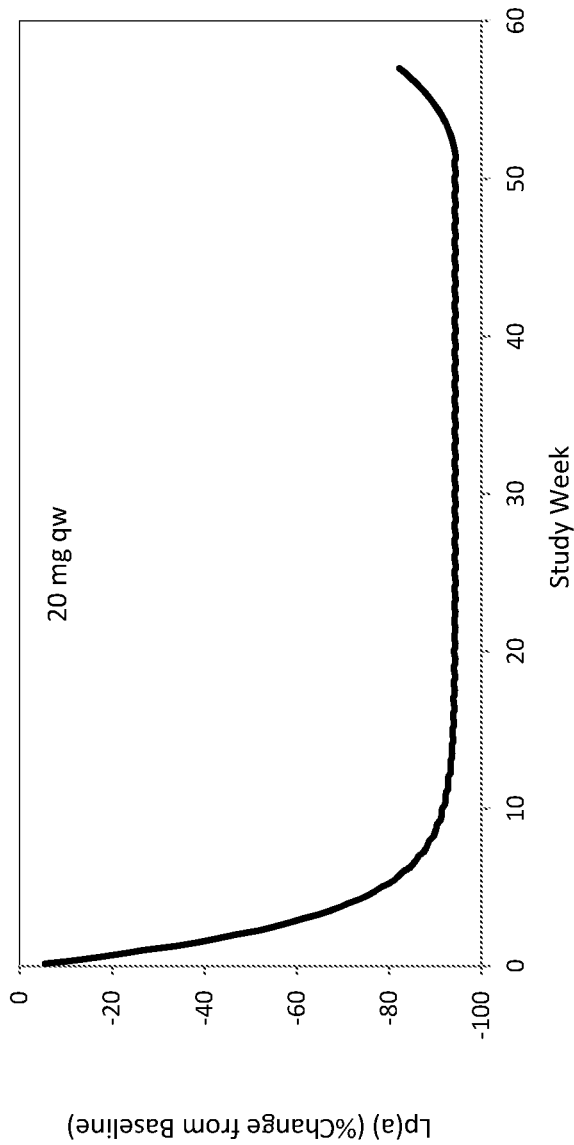
FIGS. 1A-C illustrate the predicted Lp(a) levels as a result of different weekly dosing regimens. Doses of 20 mg (FIG. 1A), 30 mg (FIG. 1B) or 40 mg (FIG. 1C) shows a steady state reduction of Lp (a) of ≥80%.

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "dosing period" means the period of time between when a human subject receives the first dose and when the human subject receives a final dose. It is envisaged that dosing of the patient may continue after the end of the dosing period, such that a first dosing period is followed by one or more further dosing periods during which the same of a different dosing regimen is used. For example, a human subject may receive 6 doses in a first dosing period where the first and last dose are given 4 weeks apart. Subsequently, the human subject may then start a second dosing period where the human subject receives doses at regular intervals (e.g. one unit dose per week, one unit dose per month, or one unit dose per quarter).

As used herein, the term "unit dose" refers to the specific amount of the oligomeric compound administered to the human at a particular time point (e.g. the specific amount of the oligomeric compound administered to the human in a single subcutaneous injection). Each unit dose forms part of a multi-dose regimen, as described herein.

As used herein, the term "unit dosage form" denotes the physical form in which each unit dose is presented for administration.

As used here, the term "sterile liquid" means and liquid suitable for administration to a human subject. In certain embodiments, sterile liquids comprise liquids that are substantially free from viable microorganisms or bacteria. In certain embodiments, sterile liquids comprise USP grade water or USP grade saline.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified. As used herein, "nucleobase sequence" means the order of contiguous nucleobases independent of any sugar, linkage, or nucleobase modification.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom. Phosphorus linking groups include without limitation groups having the formula:

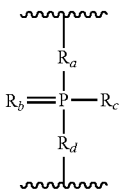

wherein:

$R_a$ and $R_d$ are each, independently, O, S, $CH_2$, NH, or $NJ_1$ wherein $J_1$ is $C_1$-$C_6$ alkyl or substituted $C_1$-$C_6$ alkyl;

$R_b$ is O or S;

$R_c$ is OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $J_1$ is $R_b$ is O or S.

Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

As used herein, "neutral linking group" means a linking group that is not charged. Neutral linking groups include without limitation phosphotriesters, methylphosphonates, MMI (—$CH_2$—N($CH_3$)—O—), amide-3 (—$CH_2$—C(=O)—N(H)—), amide-4 (—$CH_2$—N(H)—C(=O)—), formacetal (—O—$CH_2$—O—), and thioformacetal (—S—$CH_2$—O—). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and $CH_2$ component parts.

As used herein, "internucleoside neutral linking group" means a neutral linking group that directly links two nucleosides.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids. In certain embodiments, an oligomeric compound comprises a backbone of one or more linked monomeric subunits where each linked monomeric subunit is directly or indirectly attached to a heterocyclic base moiety. In certain embodiments, oligomeric compounds may also include monomeric subunits that are not linked to a heterocyclic base moiety, thereby providing abasic sites.

In certain embodiments, the linkages joining the monomeric subunits, the sugar moieties or surrogates and the heterocyclic base moieties can be independently modified. In certain embodiments, the linkage-sugar unit, which may or may not include a heterocyclic base, may be substituted with a mimetic such as the monomers in peptide nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linker" or "linker" in the context of a conjugate group means a portion of a conjugate group comprising any atom or group of atoms and which covalently link (1) an oligonucleotide to another portion of the conjugate group or (2) two or more portions of the conjugate group.

Conjugate groups are shown herein as radicals, providing a bond for forming covalent attachment to an oligomeric compound such as an antisense oligonucleotide. In certain embodiments, the point of attachment on the oligomeric compound is the 3'-oxygen atom of the 3'-hydroxyl group of the 3' terminal nucleoside of the oligomeric compound. In certain embodiments the point of attachment on the oligomeric compound is the 5'-oxygen atom of the 5'-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and a carbohydrate cluster portion, such as a GalNAc cluster portion. Such carbohydrate cluster portion comprises: a targeting moiety and, optionally, a conjugate linker. In certain embodiments, the carbohydrate cluster portion is identified by the number and identity of the ligand. For example, in certain embodiments, the carbohydrate cluster portion comprises 3 GalNAc groups and is designated "GalNAc$_3$". Specific carbohydrate cluster portions (having specific tether, branching and conjugate linker groups) are described herein and designated by Roman numeral followed by subscript "a". Accordingly "GalNac3-1$_a$" refers to a specific carbohydrate cluster portion of a conjugate group having 3 GalNac groups and specifically identified tether, branching and linking groups. Such carbohydrate cluster fragment is attached to an oligomeric compound via a cleavable moiety, such as a cleavable bond or cleavable nucleoside.

As used herein, "cleavable moiety" means a bond or group that is capable of being split under physiological conditions. In certain embodiments, a cleavable moiety is cleaved inside a cell or sub-cellular compartments, such as a lysosome. In certain embodiments, a cleavable moiety is cleaved by endogenous enzymes, such as nucleases. In certain embodiments, a cleavable moiety comprises a group of atoms having one, two, three, four, or more than four cleavable bonds.

As used herein, "cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

As used herein, "carbohydrate cluster" means a compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "single-stranded" means an oligomeric compound that is not hybridized to its complement and which lacks sufficient self-complementarity to form a stable self-duplex.

As used herein, "double stranded" means a pair of oligomeric compounds that are hybridized to one another or a single self-complementary oligomeric compound that forms a hairpin structure. In certain embodiments, a double-stranded oligomeric compound comprises a first and a second oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity includes modulation of the amount or activity of a target nucleic acid transcript (e.g. mRNA). In certain embodiments, antisense activity includes modulation of the splicing of pre-mRNA.

As used herein, "RNase H based antisense compound" means an antisense compound wherein at least some of the antisense activity of the antisense compound is attributable to hybridization of the antisense compound to a target nucleic acid and subsequent cleavage of the target nucleic acid by RNase H.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize to result in a desired antisense activity. Antisense oligonucleotides have sufficient complementarity to their target nucleic acids to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "chemical motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified.

Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein the term "metabolic disorder" means a disease or condition principally characterized by dysregulation of metabolism—the complex set of chemical reactions associated with breakdown of food to produce energy.

As used herein, the term "cardiovascular disorder" means a disease or condition principally characterized by impaired function of the heart or blood vessels.

As used herein, "prodrug" means an inactive or less active form of a compound which, when administered to a subject, is metabolized to form the active, or more active, compound (e.g., drug).

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

As used herein, "5' target site" refers to the nucleotide of a target nucleic acid which is complementary to the 5'-most nucleotide of a particular antisense compound.

As used herein, "About" means within ±10% of a value. For example, if it is stated, "a marker may be increased by about 50%", it is implied that the marker may be increased between 45%-55%.

As used herein, "administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

As used herein, "administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

As used herein, "agent" means an active substance that can provide a therapeutic benefit when administered to an animal. "First agent" means a therapeutic compound of the invention. For example, a first agent can be an antisense oligonucleotide targeting apo(a). "Second agent" means a second therapeutic compound of the invention (e.g. a second antisense oligonucleotide targeting apo(a)) and/or a non-apo (a) therapeutic compound.

As used herein, "amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

As used herein, "apo(a)" means any nucleic acid or protein sequence encoding apo(a). For example, in certain embodiments, apo(a) includes a DNA sequence encoding apo(a), a RNA sequence transcribed from DNA encoding apo(a) (including genomic DNA comprising introns and exons), a mRNA sequence encoding apo(a), or a peptide sequence encoding apo(a).

As used herein, "apo(a) nucleic acid" means any nucleic acid encoding apo(a). For example, in certain embodiments, an apo(a) nucleic acid includes a DNA sequence encoding apo(a), a RNA sequence transcribed from DNA encoding apo(a) (including genomic DNA comprising introns and exons), and a mRNA sequence encoding apo(a).

As used herein, "apo(a) mRNA" means a mRNA encoding an apo(a) protein.

As used herein, "apo(a) protein" means any protein sequence encoding Apo(a).

As used herein, "apo(a) specific inhibitor" refers to any agent capable of specifically inhibiting the expression of an apo(a) nucleic acid and/or apo(a) protein. For example, apo(a) specific inhibitors include nucleic acids (including antisense compounds), peptides, antibodies, small molecules, and other agents capable of inhibiting the expression of apo(a) nucleic acid and/or apo(a) protein. In certain embodiments, by specifically modulating apo(a) nucleic acid expression and/or apo(a) protein expression, apo(a) specific inhibitors can affect other components of the lipid transport system including downstream components. Similarly, in certain embodiments, apo(a) specific inhibitors can affect other molecular processes in an animal.

As used herein, "atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

As used herein, "coronary heart disease (CHD)" means a narrowing of the small blood vessels that supply blood and oxygen to the heart, which is often a result of atherosclerosis.

As used herein, "diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

As used herein, "diabetic dyslipidemia" or "type 2 diabetes with dyslipidemia" means a condition characterized by Type 2 diabetes, reduced HDL-C, elevated triglycerides (TG), and elevated small, dense LDL particles.

As used herein, "diluent" means an ingredient in a composition that lacks pharmacological activity, but is pharmaceutically necessary or desirable. For example, the diluent in an injected composition can be a liquid, e.g. saline solution.

As used herein, "dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

As used herein, "dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

As used herein, "effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

As used herein, "fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

As used herein, "glucose" is a monosaccharide used by cells as a source of energy and inflammatory intermediate. "Plasma glucose" refers to glucose present in the plasma.

As used herein, "high density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

As used herein, "HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

As used herein, "hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

As used herein, "hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

As used herein, "hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ*, 2007, 176:1113-1120).

As used herein, "identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

As used herein, "improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

As used herein, "increasing HDL" or "raising HDL" means increasing the level of HDL in an animal after administration of at least one compound of the invention, compared to the HDL level in an animal not administered any compound.

As used herein, "individual" or "subject" means a human selected for treatment or therapy.

As used herein, "individual in need thereof" refers to a human or non-human animal selected for treatment or therapy that is in need of such treatment or therapy.

As used herein, "induce", "inhibit", "potentiate", "elevate", "increase", "decrease", "reduce" or the like denote quantitative differences between two states. For example, "an amount effective to inhibit the activity or expression of apo(a)" means that the level of activity or expression of apo(a) in a treated sample will differ from the level of apo(a) activity or expression in an untreated sample. Such terms are applied to, for example, levels of expression, and levels of activity.

As used herein, "inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

As used herein, "inhibiting the expression or activity" refers to a reduction or blockade of the expression or activity of a RNA or protein and does not necessarily indicate a total elimination of expression or activity.

As used herein, "insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

As used herein, "insulin sensitivity" is a measure of how effectively an individual processes glucose. An individual having high insulin sensitivity effectively processes glucose whereas an individual with low insulin sensitivity does not effectively process glucose.

As used herein, "lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time.

As used herein, "lipid-lowering therapy" or "lipid lowering agent" means a therapeutic regimen provided to a subject to reduce one or more lipids in a subject. In certain embodiments, a lipid-lowering therapy is provided to reduce one or more of apo(a), CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

As used herein, "lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

As used herein, "Lp(a)" comprises apo(a) and a LDL like particle containing apoB. The apo(a) is linked to the apoB by a disulfide bond.

As used herein, "low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

As used herein, "major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

As used herein, "metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

As used herein, "metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

As used herein, "pharmaceutical agent" means a substance that provides a therapeutic benefit when administered to an individual. For example, in certain embodiments, an antisense oligonucleotide targeted to apo(a) is a pharmaceutical agent.

As used herein, "pharmaceutical composition" or "composition" means a mixture of substances suitable for administering to an individual. For example, a pharmaceutical composition can comprise one or more active agents and a pharmaceutical carrier e.g., a sterile aqueous solution.

As used herein, "pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

As used herein, "pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

As used herein, "portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

As used herein, "prevent" or "preventing" refers to delaying or forestalling the onset or development of a disease, disorder, or condition for a period of time from minutes to indefinitely. Prevent also means reducing risk of developing a disease, disorder, or condition.

As used herein, "raise" means to increase in amount. For example, to raise plasma HDL levels means to increase the amount of HDL in the plasma.

As used herein, "reduce" means to bring down to a smaller extent, size, amount, or number. For example, to reduce plasma triglyceride levels means to bring down the amount of triglyceride in the plasma.

As used herein, "region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apo(a) can be obtained by accession number from sequence databases such as NCBI and such information is incorporated herein by reference. In certain embodiments, a target region may encompass the sequence from a 5' target site of one target segment within the target region to a 3' target site of another target segment within the target region.

As used herein, "second agent" or "second therapeutic agent" means an agent that can be used in combination with a "first agent". A second therapeutic agent can include, but is not limited to, antisense oligonucleotides targeting apo(a) or apoB. A second agent can also include anti-apo(a) antibodies, apo(a) peptide inhibitors, cholesterol lowering agents, lipid lowering agents, glucose lowering agents and anti-inflammatory agents.

As used herein, "segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

As used herein, "statin" means an agent that inhibits the activity of HMG-CoA reductase.

As used herein, "subcutaneous administration" means administration just below the skin.

As used herein, "subject" means a human selected for treatment or therapy.

As used herein, "symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

As used herein, "targeting" or "targeted" means the process of design and selection of an antisense compound that will specifically hybridize to a target nucleic acid and induce a desired effect.

As used herein, "therapeutically effective amount" means an amount of a pharmaceutical agent that provides a therapeutic benefit to an individual.

As used herein, "therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

As used herein, "treat" or "treating" refers to administering a compound described herein to effect an alteration or improvement of a disease, disorder, or condition.

As used herein, "prevent" or "preventing" refers inhibit or delay one or more symptoms of a disease, disorder, or condition described herein. For example, in certain embodiments, administration of ISIS 681257 to a subject will prevent one or more symptoms of a cardiovascular disorder, e.g. administration of ISIS 681257 to a subject will inhibit or delay one or more symptoms associated with a cardiovascular disorder.

As used herein, "triglyceride" or "TG" means a lipid or neutral fat consisting of glycerol combined with three fatty acid molecules.

As used herein, "type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

Certain Embodiments

The present disclosure provides for the use of a ISIS 681257 in the manufacture of a medicament for treating, ameliorating, delaying or preventing one or more of a disease related to apo(a) and/or Lp(a). ISIS 681257 has the following structure, which includes salts thereof:

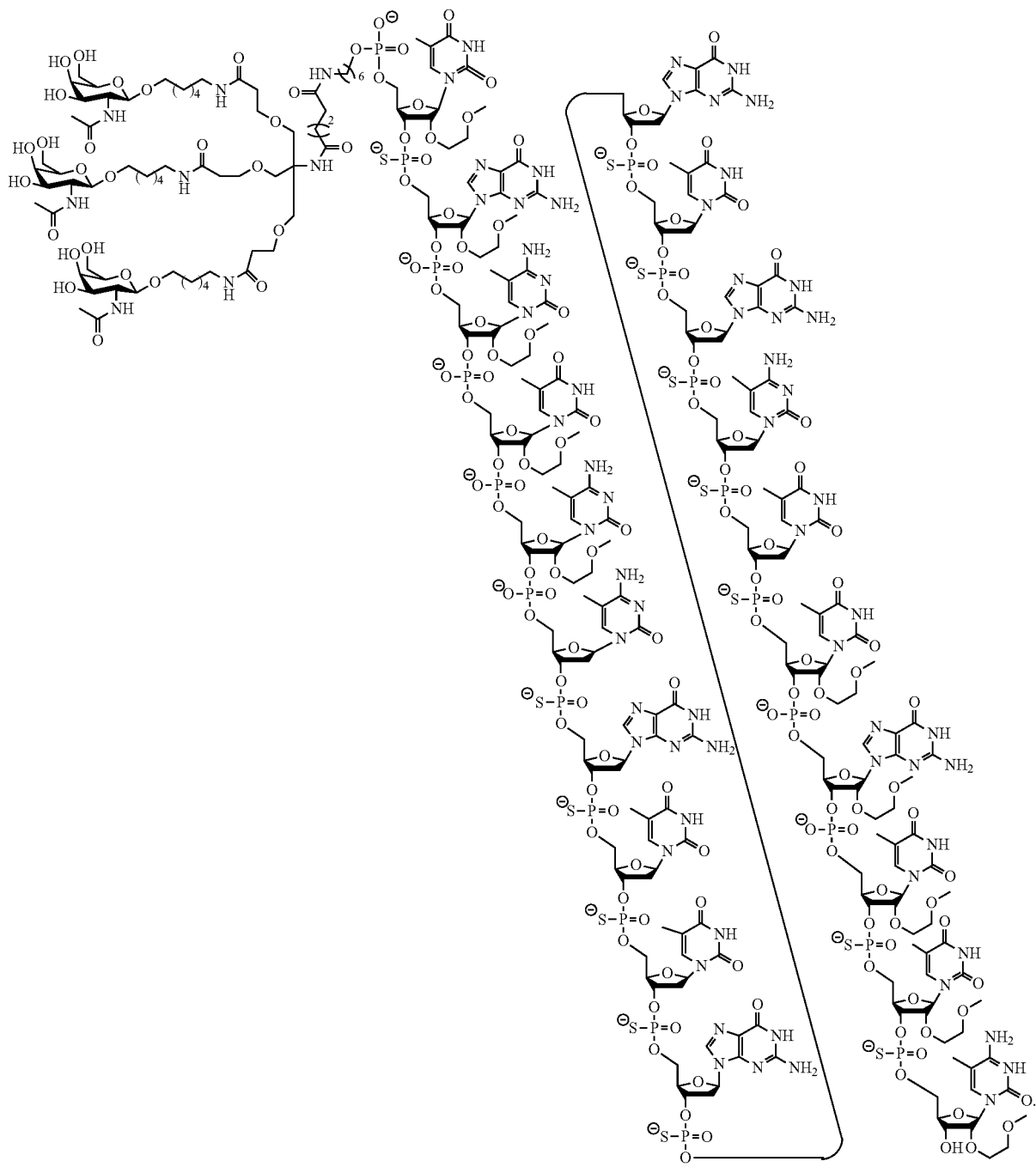

The present disclosure provides a kit for treating, preventing, or ameliorating a disease, disorder or condition as described herein wherein the kit comprises: (i) ISIS 681257; and optionally (ii) a second agent or therapy as described herein.

A kit of the present invention can further include instructions for using the kit to treat, prevent, or ameliorate a disease, disorder or condition as described herein by combination therapy as described herein.

B. Apolipoprotein (a) (Apo(a))

One apo(a) protein is linked via a disulfide bond to a single apolipoprotein B (apoB) protein to form a lipoprotein (a) (Lp(a)) particle. The apo(a) protein shares a high degree of homology with plasminogen particularly within the kringle IV type 2 repetitive domain. It is thought that the kringle repeat domain in apo(a) may be responsible for its pro-thrombotic and anti-fibrinolytic properties, potentially enhancing atherosclerotic progression. Apo(a) is transcriptionally regulated by IL-6 and in studies in rheumatoid arthritis patients treated with an IL-6 inhibitor (tocilizumab), plasma levels were reduced by 30% after 3 month treatment. Apo(a) has been shown to preferentially bind oxidized phospholipids and potentiate vascular inflammation. Further, studies suggest that the Lp(a) particle may also stimulate endothelial permeability, induce plasminogen activator inhibitor type-1 expression and activate macrophage interleukin-8 secretion. Importantly, recent genetic association studies revealed that Lp(a) was an independent risk factor for myocardial infarction, stroke, peripheral vascular disease and abdominal aortic aneurysm. Further, in the Precocious Coronary Artery Disease (PROCARDIS) study, Clarke et al. described robust and independent associations between coronary heart disease and plasma Lp(a) concentrations. Additionally, Solfrizzi et al., suggested that increased serum Lp(a) may be linked to an increased risk for Alzheimer's Disease (AD). Antisense compounds targeting apo(a) have been previously disclosed in WO2005/000201 and US2010-0331390, herein incorporated by reference in its entirety. An antisense oligonucleobase targeting Apo(a), ISIS-APOA$_{Rx}$, was assessed in a Phase I clinical trial to study it's safety profile.

Apo(a) Therapeutic Indications

The present disclosure provides methods for using ISIS 681257, which is a conjugated antisense compound targeted to an apo(a) nucleic acid for modulating the expression of apo(a) in a subject. When administered to a human, ISIS 681257 reduces expression of apo(a).

In certain embodiments, the invention provides methods for using ISIS 681257 in a pharmaceutical composition for treating a subject. In certain embodiments, the individual has an apo(a) related disease. In certain embodiments, the individual has an Lp(a) related disease. In certain embodiments, the individual has an inflammatory, cardiovascular and/or a metabolic disease, disorder or condition. In certain embodiments, the subject has an inflammatory, cardiovascular and/or metabolic disease, disorder or condition.

In certain embodiments, the cardiovascular diseases, disorders or conditions (CVD) include, but are not limited to, elevated Lp(a) associated CVD risk, recurrent cardiovascular events with elevated Lp(a), aortic stenosis (e.g., calcific aortic valve stenosis associated with high Lp(a)), aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease), stroke and the like.

In certain embodiments, ISIS 681257 modulates physiological markers or phenotypes of the cardiovascular disease, disorder or condition. For example, administration of ISIS 681257 to a human can decrease Lp(a), LDL and cholesterol levels compared to untreated subjects. In certain embodiments, the modulation of the physiological markers or phenotypes can be associated with inhibition of apo(a) by ISIS 681257.

In certain embodiments, the physiological markers of the cardiovascular disease, disorder or condition can be quantifiable. For example, Lp(a), LDL or cholesterol levels can be measured and quantified by, for example, standard lipid tests. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the cardiovascular disease, disorder or condition in a subject in need thereof. In certain embodiments, provided is a method for reducing the rate of onset of a symptom associated with the cardiovascular disease, disorder or condition. In certain embodiments, provided is a method for reducing the severity of a symptom associated with the cardiovascular disease, disorder or condition. In such embodiments, the methods comprise administering a therapeutically effective amount of ISIS 681257 to an individual in need thereof.

The cardiovascular disease, disorder or condition can be characterized by numerous physical symptoms. Any symptom known to one of skill in the art to be associated with the cardiovascular disease, disorder or condition can be prevented, treated, ameliorated or otherwise modulated with the compounds and methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the metabolic diseases, disorders or conditions include, but are not limited to, hyperglycemia, prediabetes, diabetes (type I and type II), obesity, insulin resistance, metabolic syndrome and diabetic dyslipidemia.

In certain embodiments, ISIS 681257 modulates physiological markers or phenotypes of the metabolic disease, disorder or condition. For example, administration of ISIS 681257 to humans can decrease glucose and insulin resistance levels in those subjects compared to untreated subjects. In certain embodiments, the modulation of the physiological markers or phenotypes can be associated with inhibition of apo(a) by ISIS 681257.

In certain embodiments, physiological markers of the metabolic disease, disorder or condition can be quantifiable. For example, glucose levels or insulin resistance can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity can be measured and quantified by standard tests known in the art. For such markers, in certain embodiments, the marker can be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the metabolic disease, disorder or condition in a subject in need thereof. In certain embodiments, provided is a method for reducing the rate of onset of a symptom associated with the metabolic disease, disorder or condition. In certain embodiments, provided is a method for reducing the severity of a symptom associated with the metabolic disease, disorder or condition. In such embodiments, the methods comprise administering a therapeutically effective amount of ISIS 681257 to an individual in need thereof.

The metabolic disease, disorder or condition can be characterized by numerous physical symptoms. Any symptom known to one of skill in the art to be associated with the metabolic disease, disorder or condition can be prevented, treated, ameliorated or otherwise modulated with the compounds and methods described herein. In certain embodiments, the symptom can be any of, but not limited to, excessive urine production (polyuria), excessive thirst and increased fluid intake (polydipsia), blurred vision, unexplained weight loss and lethargy.

In certain embodiments, the inflammatory diseases, disorders or conditions include, but are not limited to, elevated Lp(a) associated CVD risk, recurrent cardiovascular events with elevated Lp(a), aortic stenosis (e.g., calcific aortic valve stenosis associated with high Lp(a)), coronary artey disease (CAD), Alzheimer's Disease and thromboembolic diseases, disorder or conditions. Certain thromboembolic diseases, disorders or conditions include, but are not limited to, stroke, thrombosis, myocardial infarction and peripheral vascular disease.

In certain embodiments, ISIS 681257 modulates physiological markers or phenotypes of the inflammatory disease, disorder or condition. For example, administration of ISIS 681257 to a human can decrease inflammatory cytokine or other inflammatory markers levels in compared to untreated subjects. In certain embodiments, the modulation of the physiological markers or phenotypes can be associated with inhibition of apo(a) by ISIS 681257.

In certain embodiments, the physiological markers of the inflammatory disease, disorder or condition can be quantifiable. For example, cytokine levels can be measured and quantified by standard tests known in the art. For such markers, in certain embodiments, the marker can be decreased by at least about 5%, 10%, 15%, 20%, 25%, 30%, 35%, 40%, 45%, 50%, 55%, 60%, 65%, 70%, 75%, 80%, 85%, 90%, 95% or 99%, or a range defined by any two of these values.

Also, provided herein are methods for preventing, treating or ameliorating a symptom associated with the inflammatory disease, disorder or condition in a subject in need thereof. In certain embodiments, provided is a method for reducing the rate of onset of a symptom associated with the inflammatory disease, disorder or condition. In certain embodiments, provided is a method for reducing the severity of a symptom associated with the inflammatory disease, disorder or condition. In such embodiments, the methods comprise administering a therapeutically effective amount of ISIS 681257 to an individual in need thereof.

In certain embodiments, provided are methods of treating an individual with an apo(a) related disease, disorder or condition comprising administering a therapeutically effective amount of one or more pharmaceutical compositions as described herein. In certain embodiments, the individual has elevated apo(a) levels. In certain embodiments, provided are methods of treating an individual with an Lp(a) related disease, disorder or condition comprising administering a therapeutically effective amount of one or more pharmaceutical compositions as described herein. In certain embodiments, the individual has elevated Lp(a) levels. In certain embodiments, the individual has an inflammatory, cardiovascular and/or metabolic disease, disorder or condition. In certain embodiments, administration of a therapeutically effective amount of ISIS 681257 is accompanied by monitoring of apo(a) or Lp(a) levels. In certain embodiments, administration of a therapeutically effective amount of ISIS 681257 is accompanied by monitoring of markers of inflammatory, cardiovascular and/or metabolic disease, or other disease process associated with the expression of apo(a), to determine an individual's response to ISIS 681257. An individual's response to administration of ISIS 681257 can be used by a physician to determine the amount and duration of therapeutic intervention with the ISIS 681257.

In certain embodiments, administration of ISIS 681257 results in reduction of apo(a) expression by at least about 15%, 20%, 25%, 30%, 35%, 40%, 45%, 50%, 55%, 60%, 65%, 70%, 75%, 80%, 85%, 90%, 95% or 99%, or a range defined by any two of these values. In certain embodiments, apo(a) expression is reduced to at least ≤100 mg/dL, ≤90 mg/dL, ≤80 mg/dL, ≤70 mg/dL, ≤60 mg/dL, ≤50 mg/dL, ≤40 mg/dL, ≤30 mg/dL, ≤20 mg/dL or ≤10 mg/dL.

In certain embodiments, administration of ISIS 681257 results in reduction of Lp(a) expression by at least about 15%, 20%, 25%, 30%, 35%, 40%, 45%, 50%, 55%, 60%, 65%, 70%, 75%, 80%, 85%, 90%, 95% or 99%, or a range defined by any two of these values. In certain embodiments, Lp(a) expression is reduced to at least ≤200 mg/dL, ≤190 mg/dL, ≤180 mg/dL, ≤175 mg/dL, ≤170 mg/dL, ≤160 mg/dL, ≤150 mg/dL, ≤140 mg/dL, ≤130 mg/dL, ≤120 mg/dL, ≤110 mg/dL, ≤100 mg/dL, ≤90 mg/dL, ≤80 mg/dL, ≤70 mg/dL, ≤60 mg/dL, ≤55 mg/dL, ≤50 mg/dL, ≤45 mg/dL, ≤40 mg/dL, ≤35 mg/dL, ≤30 mg/dL, ≤25 mg/dL, ≤20 mg/dL, ≤15 mg/dL, or ≤10 mg/dL.

In certain embodiments, the invention provides methods for using ISIS 681257 in the preparation of a medicament. In certain embodiments, pharmaceutical compositions comprising ISIS 681257 are used for the preparation of a medicament for treating a patient suffering or susceptible to an inflammatory, cardiovascular and/or a metabolic disease, disorder or condition.

Apo(a) Treatment Populations

Certain subjects with high Lp(a) levels are at a significant risk of various diseases (Lippi et al., Clinica Chimica Acta, 2011, 412:797-801; Solfrizz et al.). For example, subjects will Lp(a) levels greater than ≥75 nanomoles/liter (nmol/L) or ≥30 mg/dL are considered to have increased risk for various diseases. In many subjects with high Lp(a) levels, current treatments cannot reduce their Lp(a) levels to safe levels. Apo(a) plays an important role in the formation of Lp(a), hence reducing apo(a) can reduce Lp(a) and prevent, treat or ameliorate a disease associated with Lp(a).

In certain embodiments, treatment with the compounds and methods disclosed herein is indicated for a human with elevated apo(a) levels and/or Lp(a) levels. In certain embodiments, the human has apo(a) levels≥10 mg/dL, ≥20 mg/dL, ≥30 mg/dL, ≥40 mg/dL, ≥50 mg/dL, ≥60 mg/dL, ≥70 mg/dL, ≥80 mg/dL, ≥90 mg/dL or ≥100 mg/dL. In certain embodiments, the human has Lp(a) levels≥10 mg/dL, ≥15 mg/dL, ≥20 mg/dL, ≥25 mg/dL, ≥30 mg/dL, ≥35 mg/dL, ≥40 mg/dL, ≥50 mg/dL, ≥60 mg/dL, ≥70 mg/dL, ≥80 mg/dL, ≥90 mg/dL, ≥100 mg/dL, ≥110 mg/dL, ≥120 mg/dL, ≥130 mg/dL, ≥140 mg/dL, ≥150 mg/dL, ≥160 mg/dL, ≥170 mg/dL, ≥175 mg/dL, ≥180 mg/dL, ≥190 mg/dL, ≥200 mg/dL.

In certain embodiments, the human has apo(a) levels greater than the upper limit of normal, e.g. wherein the human has apo(a) levels≥30 mg/dL, ≥35 mg/dL, ≥40 mg/dL, ≥50 mg/dL, ≥60 mg/dL, ≥70 mg/dL, ≥80 mg/dL, ≥90 mg/dL, ≥100 mg/dL, ≥110 mg/dL, ≥120 mg/dL, ≥130 mg/dL, ≥140 mg/dL, ≥150 mg/dL, ≥160 mg/dL, ≥170 mg/dL, ≥175 mg/dL, ≥180 mg/dL, ≥190 mg/dL, ≥200 mg/dL.

Certain Apo(a) Dosing Regmines

In certain embodiments, ISIS 681257 is administered to a subject in need thereof. In certain embodiments, 5 mg of ISIS 681257 is administered to a human subject. In certain embodiments, 10 mg of ISIS 681257 is administered to a human subject. In certain embodiments, 15 mg of ISIS 681257 is administered to a human subject. In certain embodiments, 20 mg of ISIS 681257 is administered to a human subject. In certain embodiments, 25 mg of ISIS 681257 is administered to a human subject. In certain embodiments, 30 mg of ISIS 681257 is administered to a human subject.

In certain embodiments, ISIS 681257 is administered to a subject in need thereof. In certain embodiments, 40 mg of ISIS 681257 is administered to a human subject. In certain embodiments, 50 mg of ISIS 681257 is administered to a human subject. In certain embodiments, 60 mg of ISIS 681257 is administered to a human subject. In certain embodiments, 70 mg of ISIS 681257 is administered to a human subject. In certain embodiments, 80 mg of ISIS 681257 is administered to a human subject. In certain embodiments, 90 mg of ISIS 681257 is administered to a human subject.

In certain embodiments, ISIS 681257 is administered to a subject in need thereof. In certain embodiments, 5 mg of ISIS 681257 is administered to a human subject during a dosing period. In certain embodiments, 10 mg of ISIS 681257 is administered to a human subject during a dosing period. In certain embodiments, 15 mg of ISIS 681257 is administered to a human subject during a dosing period. In certain embodiments, 20 mg of ISIS 681257 is administered to a human subject during a dosing period. In certain embodiments, 25 mg of ISIS 681257 is administered to a human subject during a dosing period. In certain embodiments, 30 mg of ISIS 681257 is administered to a human subject during a dosing period. In certain embodiments, the dosing period is one week. In certain embodiments, only one dose is given during the dosing period.

In certain embodiments, 5 mg of ISIS 681257 is administered to a human subject each week. In certain embodiments, 10 mg of ISIS 681257 is administered to a human subject each week. In certain embodiments, 15 mg of ISIS 681257 is administered to a human subject each week. In certain embodiments, 20 mg of ISIS 681257 is administered to a human subject each week. In certain embodiments, 25 mg of ISIS 681257 is administered to a human subject each week. In certain embodiments, 30 mg of ISIS 681257 is administered to a human subject each week. In certain embodiments, 40 mg of ISIS 681257 is administered to a human subject each week. In certain embodiments, 50 mg of ISIS 681257 is administered to a human subject each week. In certain embodiments, 60 mg of ISIS 681257 is administered to a human subject each week. In certain embodiments, 70 mg of ISIS 681257 is administered to a human subject each week. In certain embodiments, 80 mg of ISIS 681257 is administered to a human subject each week.

In certain embodiments, ISIS 681257 is administered to a subject in need thereof. In certain embodiments, 20 mg of ISIS 681257 is administered to a human subject during a dosing period. In certain embodiments, 30 mg of ISIS 681257 is administered to a human subject during a dosing period. In certain embodiments, 40 mg of ISIS 681257 is administered to a human subject during a dosing period. In certain embodiments, 50 mg of ISIS 681257 is administered to a human subject during a dosing period. In certain embodiments, 60 mg of ISIS 681257 is administered to a human subject during a dosing period. In certain embodiments, 70 mg of ISIS 681257 is administered to a human subject during a dosing period. In certain embodiments, 80 mg of ISIS 681257 is administered to a human subject during a dosing period. In certain embodiments, the dosing period is one month. In certain embodiments, the dosing period is four weeks. In certain embodiments, only one dose is given during the dosing period.

In certain embodiments, 20 mg of ISIS 681257 is administered to a human subject once every four weeks. In certain embodiments, 30 mg of ISIS 681257 is administered to a human subject once every four weeks. In certain embodiments, 40 mg of ISIS 681257 is administered to a human subject once every four weeks. In certain embodiments, 50 mg of ISIS 681257 is administered to a human subject once every four weeks. In certain embodiments, 60 mg of ISIS 681257 is administered to a human subject once every four weeks. In certain embodiments, 70 mg of ISIS 681257 is administered to a human subject once every four weeks. In certain embodiments, 80 mg of ISIS 681257 is administered to a human subject once every four weeks.

In certain embodiments, 20 mg of ISIS 681257 is administered to a human subject once every month. In certain embodiments, 30 mg of ISIS 681257 is administered to a human subject once every month. In certain embodiments, 40 mg of ISIS 681257 is administered to a human subject once every month. In certain embodiments, 50 mg of ISIS 681257 is administered to a human subject once every month. In certain embodiments, 60 mg of ISIS 681257 is administered to a human subject once every month. In certain embodiments, 70 mg of ISIS 681257 is administered to a human subject once every month. In certain embodiments, 80 mg of ISIS 681257 is administered to a human subject once every month.

C. Certain Pharmaceutical Compositions

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, the present disclosure provides methods of administering a pharmaceutical composition comprising an oligonucleotide of the present disclosure to a subject. Suitable administration routes include parenteral (e.g., intravenous, intramuscular, intramedullary, and subcutaneous).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: ISIS 681257 Clinical Trial

As described herein, a double-blinded, placebo-controlled, dose-escalation Phase 1 study was performed on healthy volunteers with elevated Lp(a) to assess safety, tolerability, pharmacokinetics (PK) and pharmacodynamics (PD) after administration of single and multiple doses of ISIS 681257. ISIS 681257 was previously disclosed in WO 2014/179625 and is also described hereinabove. ISIS 681257 has been shown to be potent in inhibiting Lp(a) and tolerable when administered to non-human subjects. This subsequent study revealed unexpectedly improved properties of ISIS 681257 when administered to human subjects.

Screening

Up to 28 days prior to treatment, subjects were screened for eligibility to participate in the study. Admission criteria for the study include the following:

1. Healthy males or females aged 18-65 inclusive and weighing ≥50 kg at the time of informed consent
2. BMI≤35.0 kg/m2
3. Subjects must have Lp(a)≥75 nanomoles/liter (nmol/L) (≥30 mg/dL) at Screening. The Lp(a) value obtained via the Lp(a) pre-screening protocol may also be used to meet this criterion if measured within 6 months of dosing.

Study Drug

Solutions of the Study Drug ISIS 681257 (100 mg/mL, 0.8 mL) contained in stoppered glass vials was used. Vials were for single use only. Doses of ISIS 681257 solution and placebo (0.9% sterile saline) were prepared by an unblinded pharmacist (or qualified delegate). A trained professional administered the ISIS 681257 or placebo blindly as a subcutaneous (sc) injection(s) in the abdomen, thigh, or outer area of the upper arm on each dosing day.

Treatment and Post-Treatment Evaluation

Subjects enrolled in the study were split into 2 treatment arms: Single Ascending Dose (SAD) or Multiple Ascending Dose (MAD).

Example 1A: Single Ascending Dose (SAD)

Approximately 28 subjects were enrolled in the SAD arm of this study, grouped into cohorts of 4 or 8 subjects randomized 3:1, ISIS 681257 to placebo. The subjects were administered placebo or ISIS 681257 at the doses listed in Table 1.

TABLE 1

Single Ascending Doses

| Cohort (n) | Dose |
|---|---|
| A (4) | 10 mg |
| B (4) | 20 mg |
| C (4) | 40 mg |
| D (8) | 80 mg |
| E (8) | 120 mg |

After treatment with a single dose of ISIS 681257 or placebo, the subjects were followed for up to 90 days to monitor the safety, tolerability, PK and PD of the drug. During the follow-up period, subjects return to the Study Center for visits on Study Days 2, 3, 8, 15 and 30 post-treatment (and Days 50, 70 and 90 post-treatment for Cohorts C, D and E) for safety and laboratory evaluations (blood draws), monitoring, concomitant medication usage recording, and adverse event (AE) collection. Collection of urine and feces was also performed on certain days. All visits by the subject for post-treatment assessment had a visit window of up to ±1 days.

Analysis of serum samples showed dose dependent reductions in Lp(a) levels after a single dose of ISIS 681257 as measured 2 days, 4 days, 8 days, 15 days and 30 days post-treatment (Cohorts C, D and E were also assessed about 50 days, 70 days and 90 days post-treatment). Results, presented as a mean percent change in Lp(a) from baseline, are shown in Table 2.

TABLE 2

Dose-dependent Change in Lp(a) after a Single Dose of ISIS 681257

% Change from Baseline

| Cohort | Day 2 | Day 4 | Day 8 | Day 15 | Day 30 | Day 50 | Day 70 | Day 90 |
|---|---|---|---|---|---|---|---|---|
| Placebo | −1.7 | −2.4 | −9.6 | 0.3 | 6.8 | −14 | −9 | 3.9 |
| A | 4 | −5 | −16 | −20 | −26 | — | — | — |
| B | 7 | 8 | 2 | −22 | −33 | — | — | — |
| C | −2 | −13 | −33 | −41 | −43 | −35 | −26 | −26 |
| D | −21 | −35 | −50 | −70 | −79 | −71 | −52 | −46 |
| E | −11 | −25 | −50 | −76 | −85 | −75 | −61 | −44 |

Additionally, analysis of apo(a) isoforms, lipoprotein-associated phospholipase A2 (Lp-PLA2), secretory phospholipase A2 (sPLA2), oxidized phospholipid associated with apolipoprotein B (OxPL-apoB), and oxidized phospholipid associated with apolipoprotein(a) (OxPL-apo(a)) were performed.

During scheduled visits to the Study Center, the safety and tolerability of ISIS 681257 was clinically assessed in the subjects. Clinical staff assessed safety and tolerability by collecting and/or measuring one or more of the following: adverse events (AEs), quality of life assessments, concomitant medication/procedure information, vital signs, physical examination results (e.g., injection site reactions (ISRs) or flu-like symptoms (FLSs)), waist circumference, skinfold measurements, DEXA scans, electrocardiograms (ECGs), liver MRIs and echocardiograms.

Laboratory measurements such as serum chemistry (e.g., ALT, AST, bilirubin, creatinine, BUN), urinalysis, coagulation (e.g., aPTT (sec), PT (sec), INR, plasminogen), complement (e.g., C5a, Bb), hematology (e.g., hematocrit, white blood cells, platelets), immune function, thyroid function, inflammation (hsCRP), lipid panel (e.g., total cholesterol, HDL, LDL, TG, apoB, VLDL), ISIS 681257 plasma trough concentrations, and/or immunogenicity testing were performed on subject samples to assess the health and safety of each subject and the PD of the drug.

Laboratory measurements of subject samples were also used for PK profiling of the drug. For example, samples were used for measuring the amount and stability of ISIS 681257 and/or metabolites thereof, assessing drug binding proteins, and/or assessing other actions of ISIS 681257 with plasma constituents.

Both single dose treatment and multiple dose treatment with ISIS 681257 did not result in any safety or tolerability issues, at any of the clinically revelant doses tested. No ISRs were observed and no side effects were noted in any laboratory tests and the liver enzymes ALT and AST were not elevated.

The above results were surprising, because earlier experiments involving both the unconjugated compound (ISIS 494372) and the GalNAc conjugated compound (ISIS 681257) had suggested that the GalNAc conjugated compound would have significantly lower potency and/or a shorter duration of action in humans than was observed following the first dosing of humans reported herein (e.g. see Examples 89, 100 and 108 of WO 2014/179625 and Tsimikas et al., Lancet, 2015 Oct. 10; 386:1472-83). In light of these surprising results, when treating humans, the GalNAc conjugated compound (ISIS 681257, or a salt thereof) can be administered at lower doses and/or less frequently than expected based on the earlier in vivo testing of the GalNAc conjugated compound. This can provide one or more very significant improvements in treating humans, e.g. reduced cost of treatment, improved patient compliance, reduced volume of administered medicinal product and/or potentially reduced risk of potential adverse events via lower dose administration regimens.

Example 1B: Multiple Ascending Dose (MAD)

Thirty subjects were enrolled in the MAD arm of this study, grouped into cohorts of 10 randomized 4:1, ISIS 681257 to placebo. The subjects were administered a placebo or ISIS 681257 at the doses listed in Table 3. A total of 6 doses of drug or placebo was administered to each subject: loading doses were administered in the first week on Study Days 1 (first dose), 3, 5 and 8; maintenance doses were then administered weekly on Study Days 15 and 22.

TABLE 3

Multiple Ascending Doses

| Cohort (n) | ISIS 681257 Dose | # of Doses | Total Drug Dose |
|---|---|---|---|
| AA (10) | 10 mg | 6 | 60 mg |
| BB (10) | 20 mg | 6 | 120 mg |
| CC (10) | 40 mg | 6 | 240 mg |

During treatment with ISIS 681257 or placebo and for up to 13 weeks after treatment, the subjects were monitored for safety, tolerability, PK and PD of the drug. During the treatment period and the follow-up period, subjects return to the Study Center for visits on Study Days 5, 8, 15, 22, 29, 36, 50, 64, 85 and 113 for safety and clinical laboratory evaluations (blood draws), monitoring, concomitant medication usage recording, and AE event collection. Collection of urine and feces was also performed on certain days. All visits by the subject for post-treatment assessment had a visit window of up to ±1 days.

Analysis of serum samples showed reductions in Lp(a) levels after multiple doses of ISIS 681257 as measured 5 days, 8 days, 15 days, 22 days, 29 days and 36 days after start of treatment. Results, presented as a mean percent change in Lp(a) from baseline, are shown in Table 4. Surprisingly, after a single dose of ISIS 681257, levels of Lp(a) continue to fall, reaching a nadir at about day 50 for the AA cohort. This demonstrates that the effective half life of ISIS 681257 appears to be much longer than anticipated. Additionally, cohorts BB and CC demonstrate continued reduction in Lp(a) through 36 days after administration of ISIS 681257.

performed. The results showed a significant reduction in LDL cholesterol, apolipoprotein B (apoB), and oxidised phospholipids (OxPL) associated with apoB and apo(a). Therefore, the reductions in Lp(a) occurred alongside significant reductions in proinflammatory OxPL, as well as reductions in LDL-C and apoB-100, which is consistent with a salutary effect on several causal pathways that mediate cardiovascular disease and calcific aortic valve stenosis. See Viney, et al. Lancet, 2016, September 2016; 388: 2239-53.

During scheduled visits to the Study Center, the safety and tolerability of ISIS 681257 was clinically assessed in the subjects. Clinical staff assessed safety and tolerability by collecting and/or measuring one or more of the following: adverse events (AEs), quality of life assessments, concomitant medication/procedure information, vital signs, physical examination results (e.g., injection site reactions (ISRs) or flu-like symptoms (FLSs)), waist circumference, skinfold measurements, DEXA scans, electrocardiograms (ECGs), liver MRIs and echocardiograms.

Laboratory measurements such as serum chemistry (e.g., ALT, AST, bilirubin, creatinine, BUN), urinalysis, coagulation (e.g., aPTT (sec), PT (sec), INR, plasminogen), comple-

TABLE 4

Dose-dependent Reduction in Lp(a) after a Multiple Doses of ISIS-681257

| Cohort | % Change from Baseline | | | | | | | | | |
|---|---|---|---|---|---|---|---|---|---|---|
| | Day 5 | Day 8 | Day 15 | Day 22 | Day 29 | Day 36 | Day 50 | Day 64 | Day 85 | Day 113 |
| Placebo | −2.6 | −11 | −11 | −4 | −3 | −10 | −1 | 18 | −1 | 10 |
| AA | −9 | −23 | −43 | −50 | −61 | −72 | −68 | −66 | −52 | −39 |
| BB | −10 | −20 | −52 | −68 | −75 | −80 | −80 | −77 | −64 | −52 |
| CC | −19 | −44 | −71 | −84 | −90 | −94 | −90 | −85 | −73 | −58 |

TABLE 5

ED50 Values in Human

| Regimen | ISIS 494372 | ISIS 681257 |
|---|---|---|
| Weekly Dose ED50 | 145 mg (1.5 ml) | 4.5 mg (0.05 ml) |

In human subjects, ISIS 681257 displayed dose-dependent, durable, statistically significant reductions in Lp(a) and an ED50 of 4.5 mg. ISIS 681257 was unexpectedly found to be ≥30-fold more potent than ISIS 494372 (an unconjugated antisense compound of the same nucleobase sequence and length; previously described in WO 2013/177468). Earlier experiments involving both ISIS 494372 and ISIS 681257 (reported in WO 2014/179625) had indicated that the GalNAc conjugated compound benefits from higher in vivo potency in mice, but these earlier experiments did not reveal or predict the unexpected ≥30-fold improvement in humans. Additionally, for the 10 mg multi-dose cohort, data points past Day 36 indicate that the nadir of Lp(a) levels for 6 of the 8 patients was not achieved until about Day 50, indicating that in humans ISIS 681257 showed an unexpected long half-life (T½) compared to ISIS 494372 (Tsimikas et al., Lancet, 2015 Oct. 10; 386:1472-83) and this was likewise not revealed or predicted by earlier experiments in mice involving both ISIS 494372 and ISIS 681257.

Additionally, analysis of apo(a) isoforms, lipoprotein-associated phospholipase A2 (Lp-PLA2), secretory phospholipase A2 (sPLA2), oxidized phospholipid associated with apolipoprotein B (OxPL-apoB), and oxidized phospholipid associated with apolipoprotein(a) (OxPL-apo(a)) were ment (e.g., C5a, Bb), hematology (e.g., hematocrit, white blood cells, platelets), immune function, thyroid function, inflammation (hsCRP), lipid panel (e.g., total cholesterol, HDL, LDL, TG, apoB, VLDL), ISIS 681257 plasma trough concentrations, and/or immunogenicity testing were performed on subject samples to assess the health and safety of each subject and the PD of the drug.

Laboratory measurements of subject samples were also used for PK profiling of the drug. For example, samples were used for measuring the amount and stability of ISIS 681257 and/or metabolites thereof, assessing drug binding proteins, and/or assessing other actions of ISIS 681257 with plasma constituents.

Multiple dose treatments with ISIS 681257 did not result in any safety or tolerability issues. No ISR or FLS were observed. Liver enzymes ALT and AST were not elevated.

The ≥30-fold improvement in potency in humans was significantly greater than that expected. The above results were surprising, because earlier experiments involving both the unconjugated compound (ISIS 494372) and the GalNAc conjugated compound (ISIS 681257) had suggested that the GalNAc conjugated compound would have significantly lower potency and/or a shorter duration of action in humans than was observed following the first dosing of humans reported herein (e.g. see Examples 89, 100 and 108 of WO 2014/179625 and Tsimikas et al., Lancet, 2015 Oct. 10; 386:1472-83). In light of these surprising results, when treating humans, the GalNAc conjugated compound (ISIS 681257, or a salt thereof) can be administered at lower doses and/or less frequently than expected based on the earlier in vivo testing of the GalNAc conjugated compound. This can provide one or more very significant improvements in treating humans, e.g. reduced cost of treatment, improved patient compliance, reduced volume of administered medicinal product and/or potentially reduced risk of potential adverse events via lower dose administration regimens.

Example 2: Dose Regimens

Figure 1B:
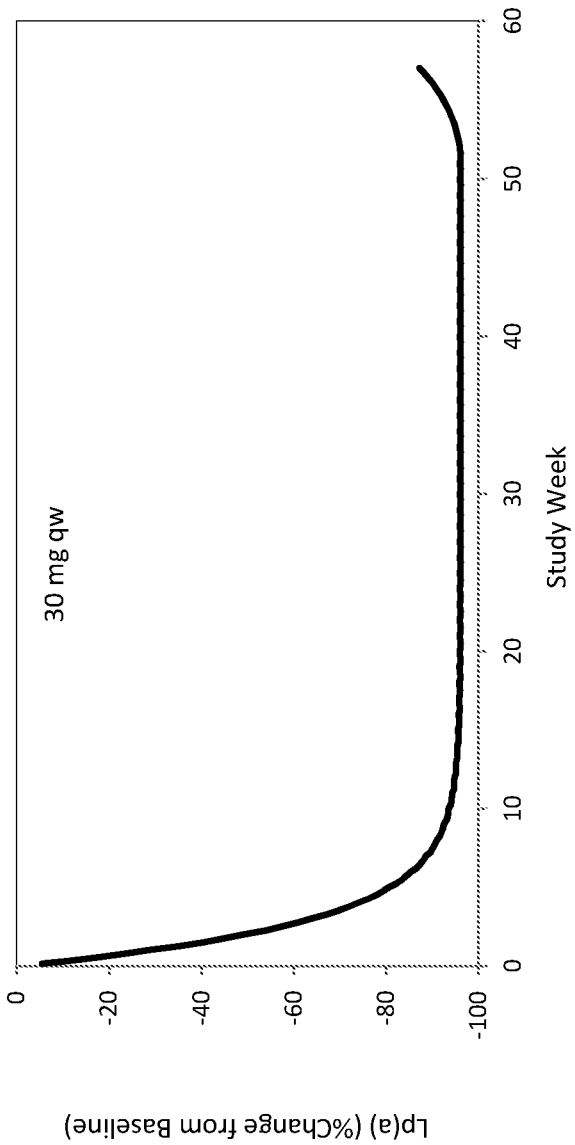
Figure 1C:
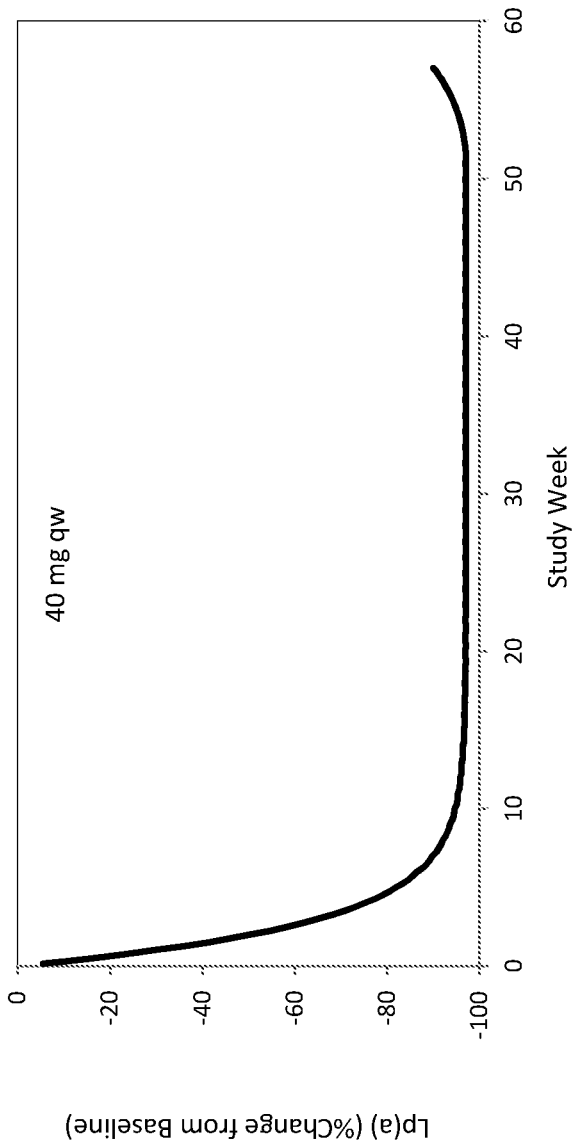
Figure 2A:
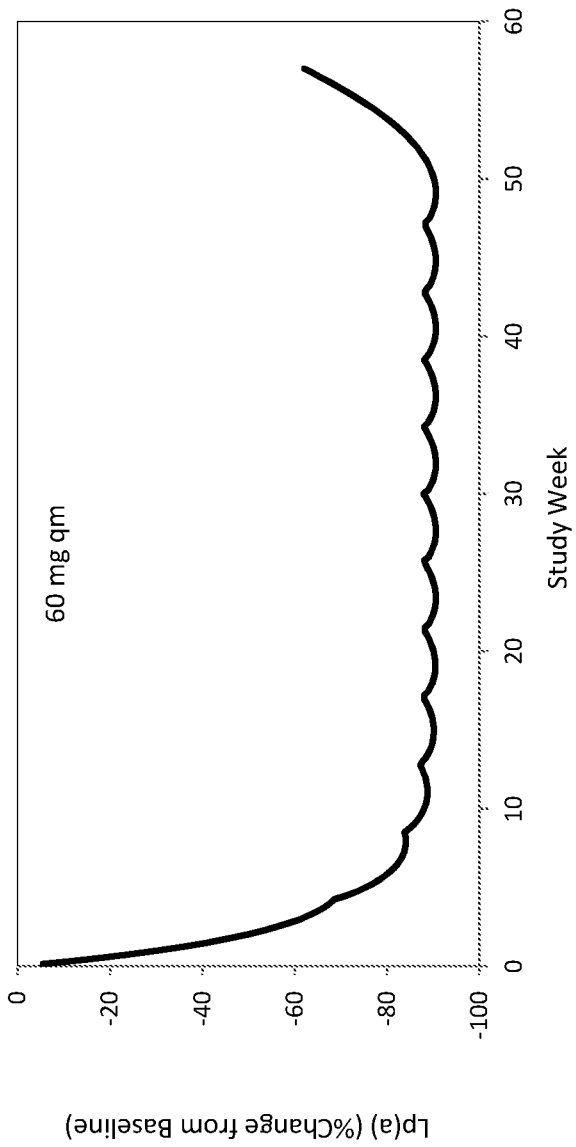
FIGS. 2A-B illustrate the predicted Lp(a) levels as a result of different monthly dosing regimens. Doses of 60 mg (FIG. 2A) and 80 mg (FIG. 2B) Lp(a) show a steady state reduction of Lp (a) of about 80%.
Figure 2B:
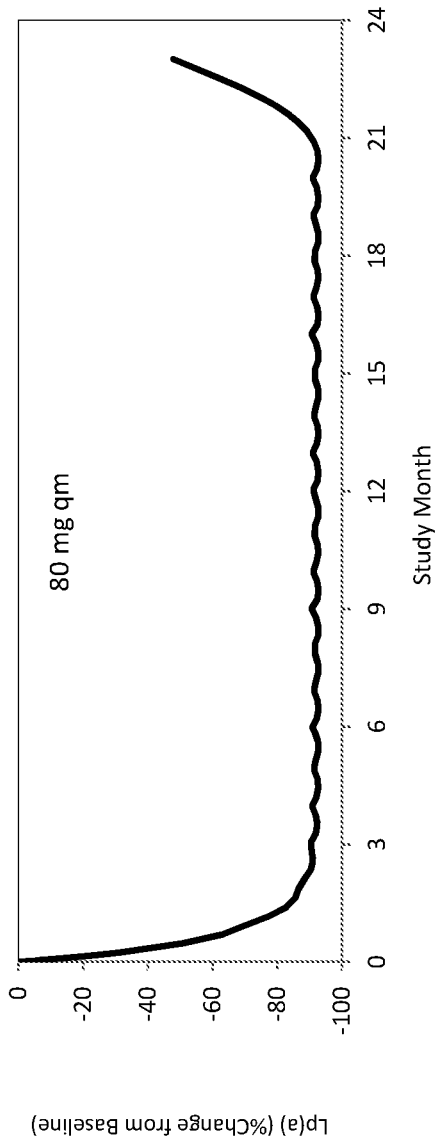

Modeling based on the ongoing Phase 1 clinical trial results was performed to assess optimal clinical dose regimens for ISIS 681257.
Weekly Dosing
FIGS. 1A-C. Predicted Weekly Dosing Regimens. Charts are shown modeling the effect on Lp(a) by weekly administration of ISIS 681257 at doses of 20 mg (FIG. 1A), 30 mg (FIG. 1B) or 40 mg (FIG. 1C). Lp(a) shows a steady state reduction of ≥80%.
Monthly Dosing
FIGS. 2A-B. Predicted Monthly Dosing Regimens. Chart are shown modeling the effect on Lp(a) by monthly administration of ISIS 681257 at dose of 60 mg (FIG. 2A) and 80 mg (FIG. 2B). Lp(a) shows a steady state reduction of about 80%.
Two Months Dosing
FIG. 3. Predicted 2-month Dosing Regimen. A chart is shown modeling the effect on Lp(a) by administration of ISIS 681257 at an 80 mg dose every 2-months. Lp(a) shows a steady state reduction of about 80%.
Quarterly Dosing
FIG. 4. Predicted Quarterly Dosing Regimen. A chart is shown modeling the effect on Lp(a) by quarterly administration of ISIS 681257 at an 80 mg dose. Lp(a) shows a steady state reduction of 80% and maximum reduction of >90%.

Example 3: Dose Regimens

Figure 5A:
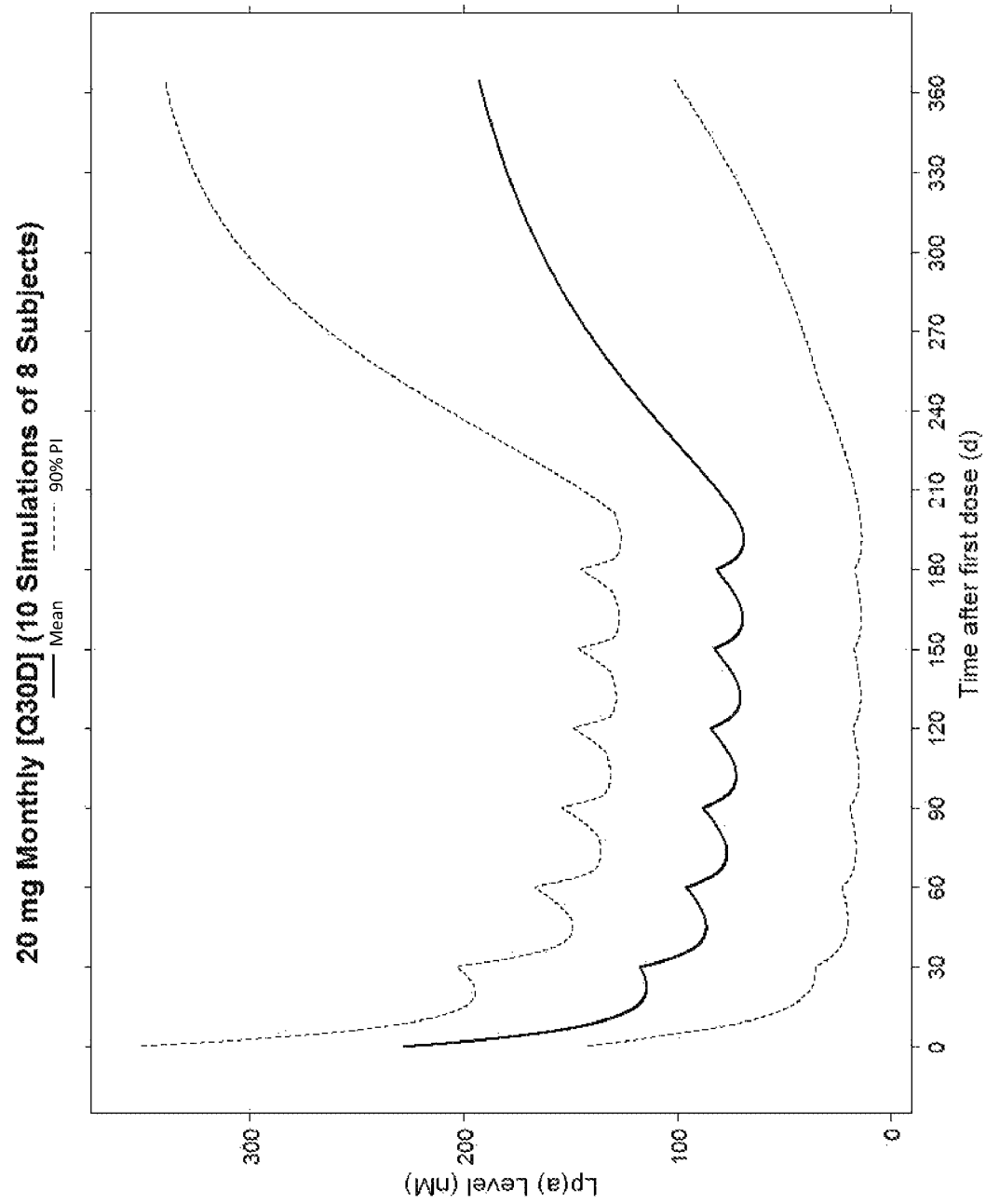
FIGS. 5A-D illustrate the predicted Lp(a) levels as a result of different monthly dosing regimens. Figures are shown modeling the effect on Lp(a) by monthly administration of ISIS 681257 at doses of 20 mg (FIG. 5A), 40 mg (FIG. 5B), 60 mg (FIG. 5C), and 80 mg (FIG. 5D). The dark middle line represents the predicted dose, while the uppermost and lowermost lines represent the 90% Confidence Interval.
Figure 5B:
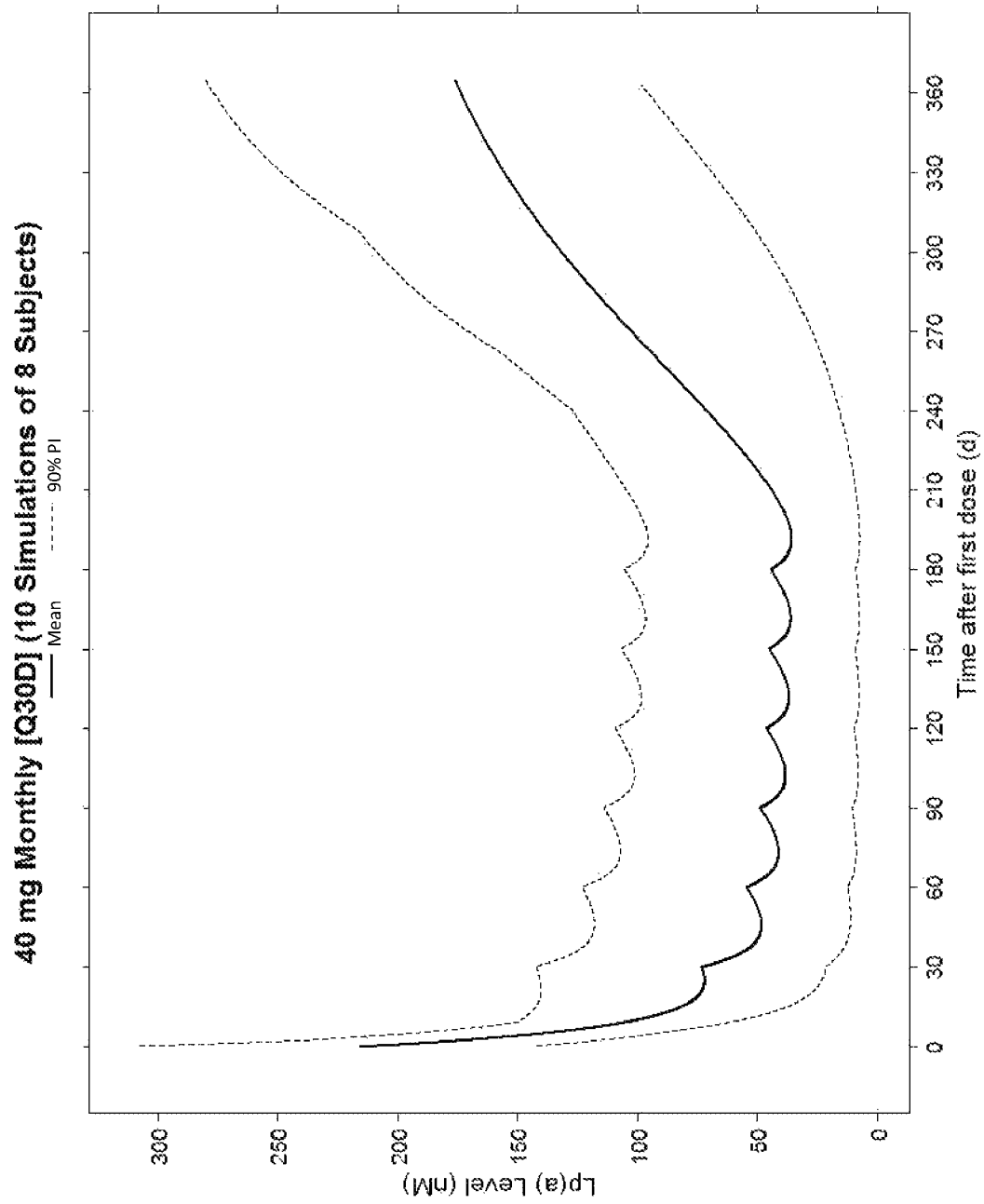
Figure 5C:
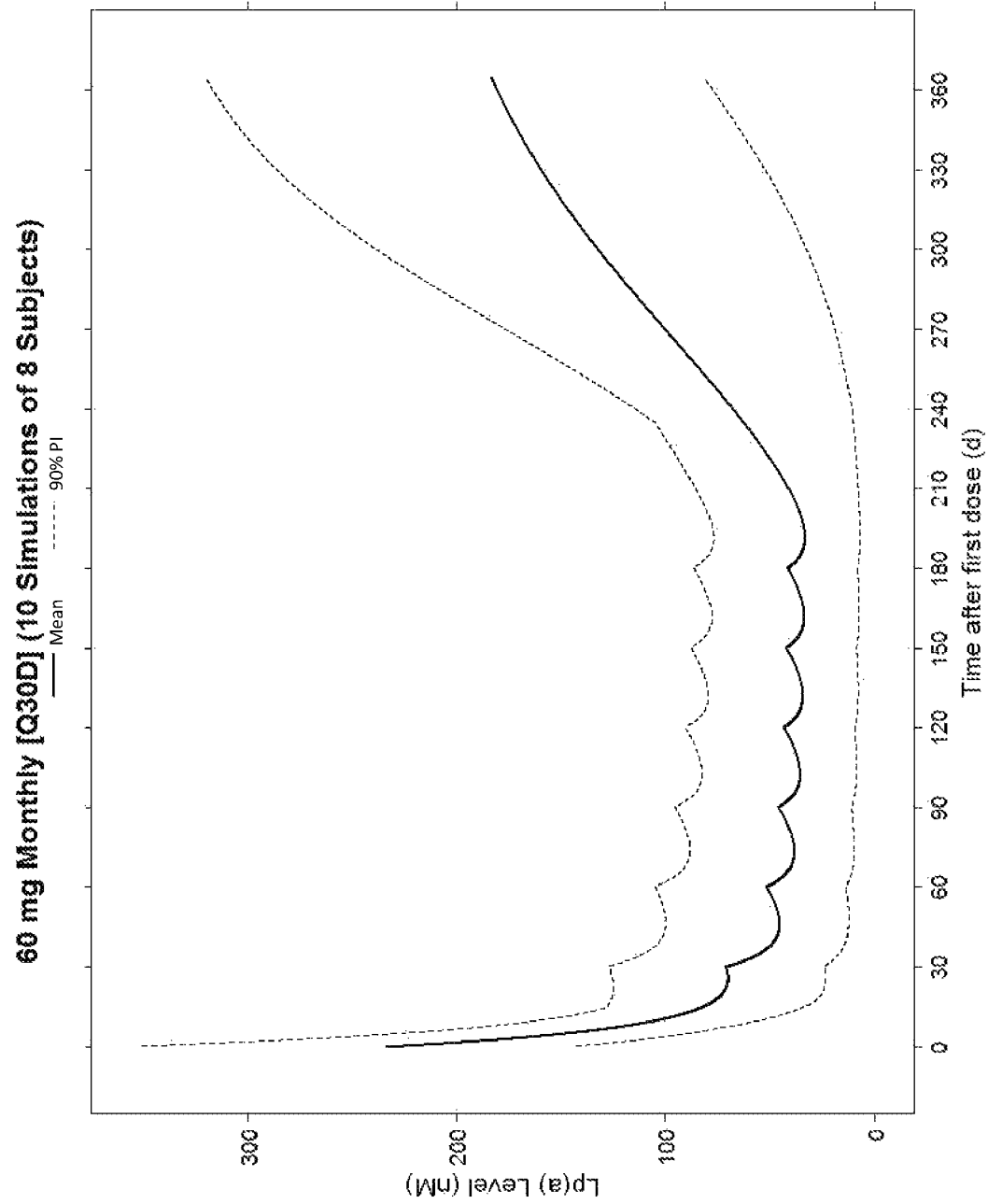
Figure 5D:
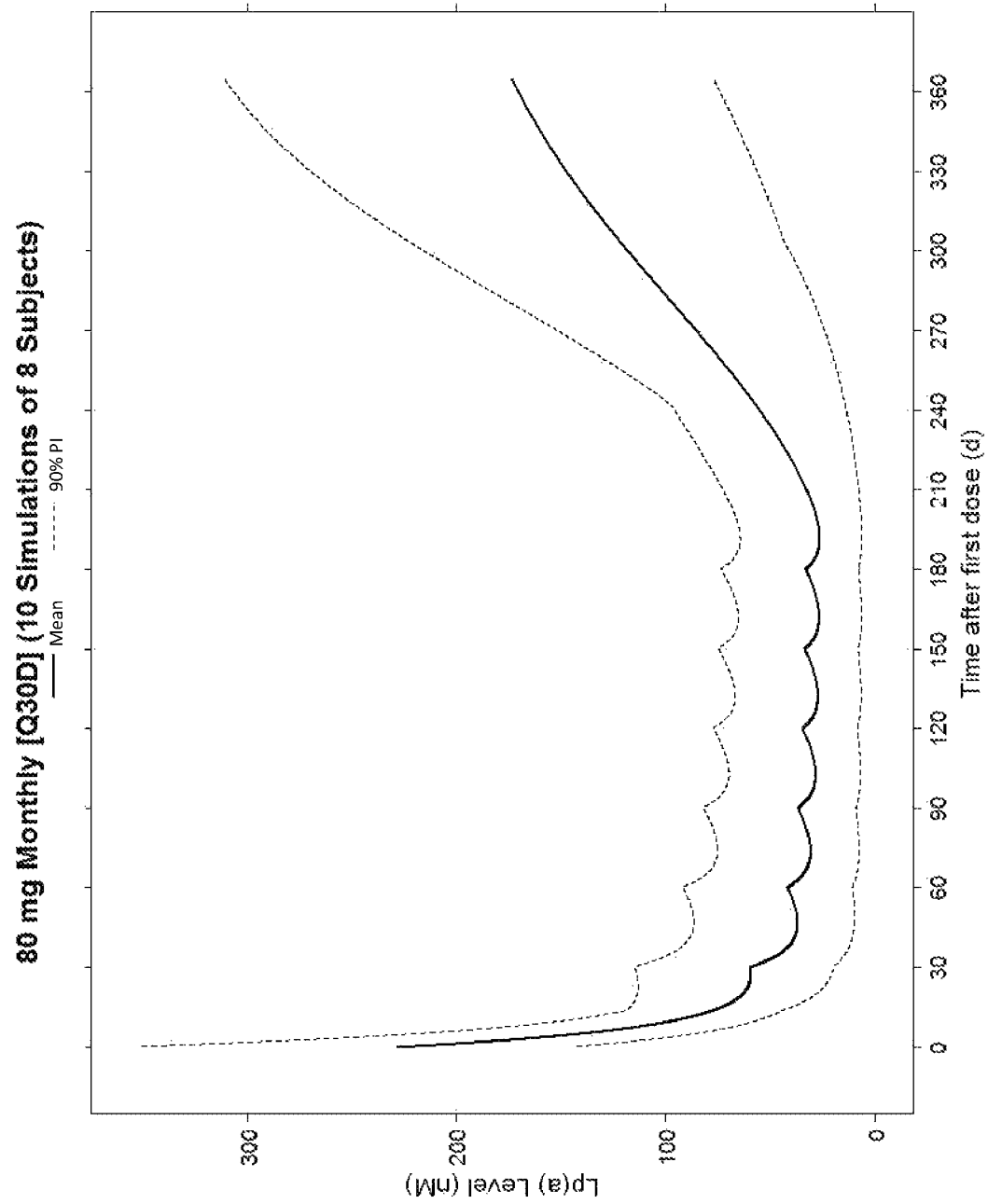
Figure 6A:
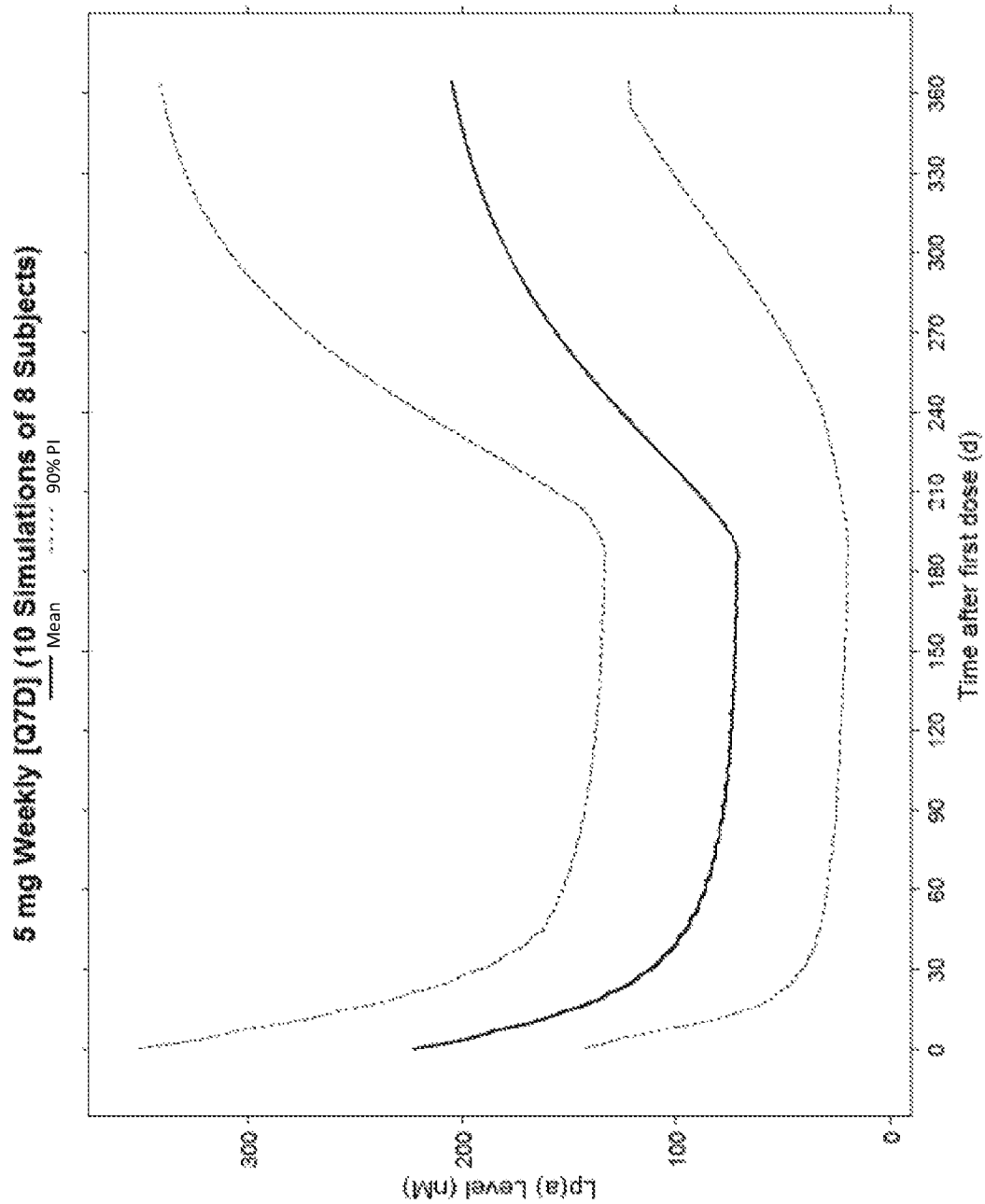
FIGS. 6A-D illustrate the predicted Lp(a) levels as a result of different weekly dosing regimens.
Figure 6B:
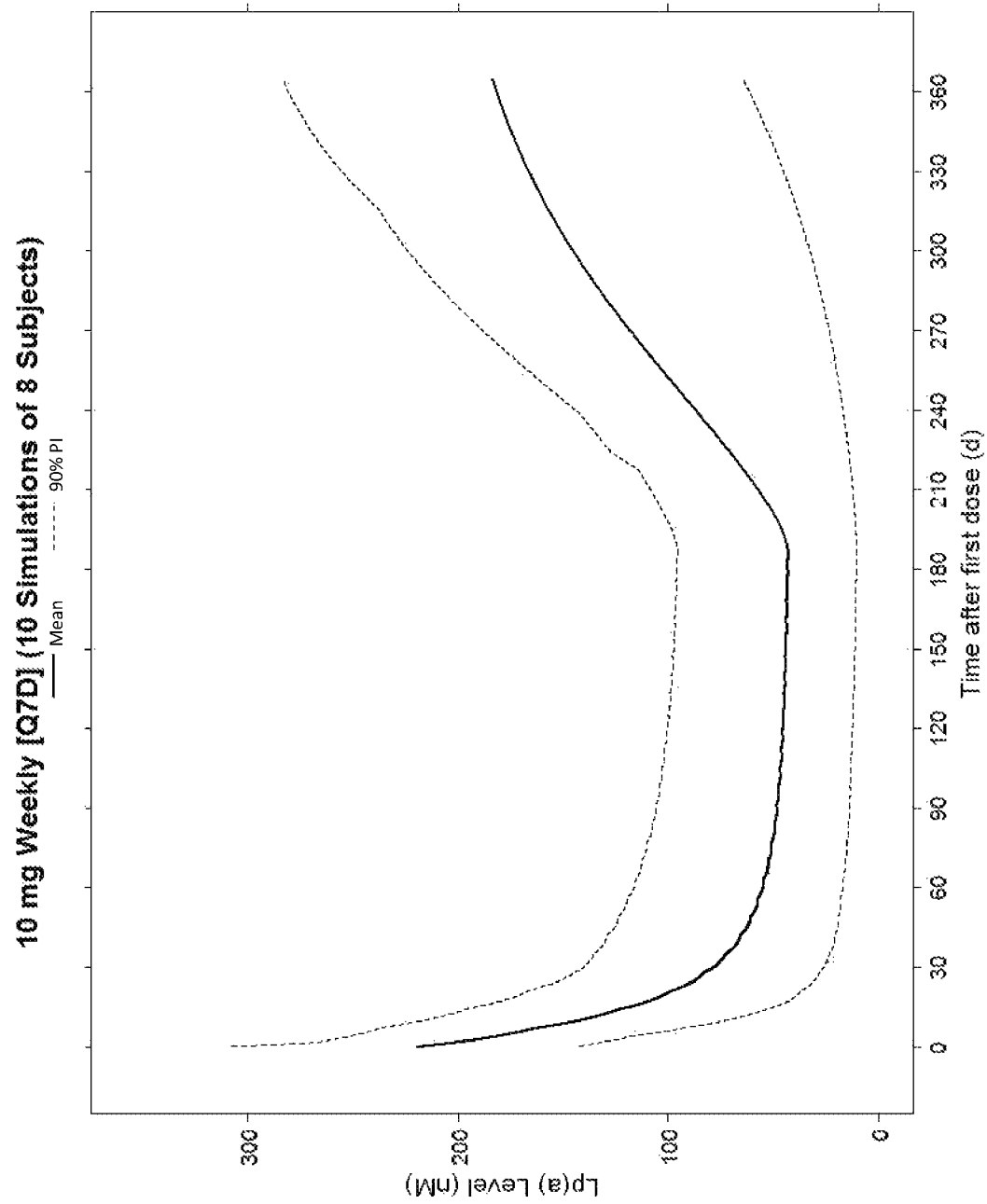
Figure 6C:
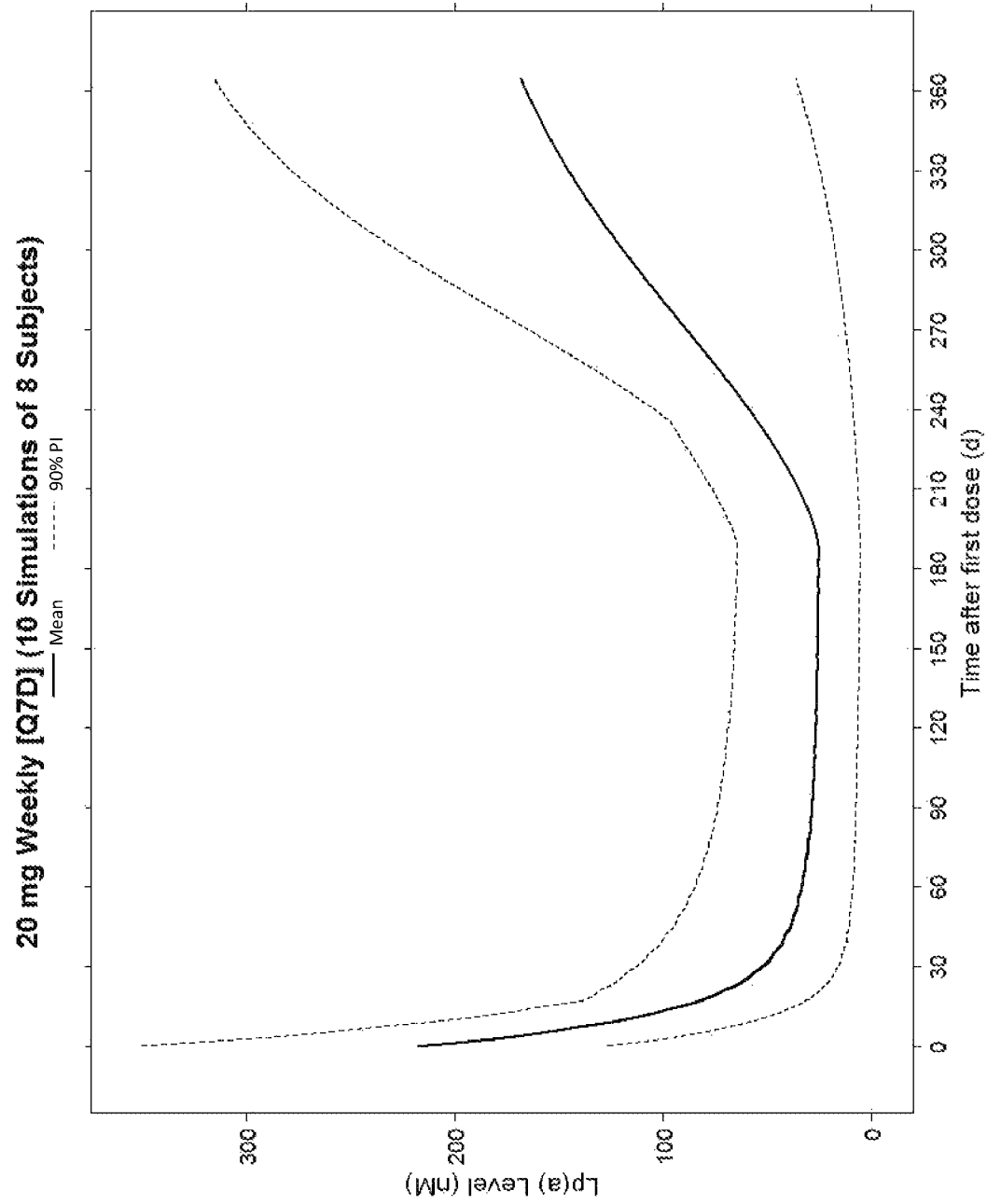
Figure 6D:
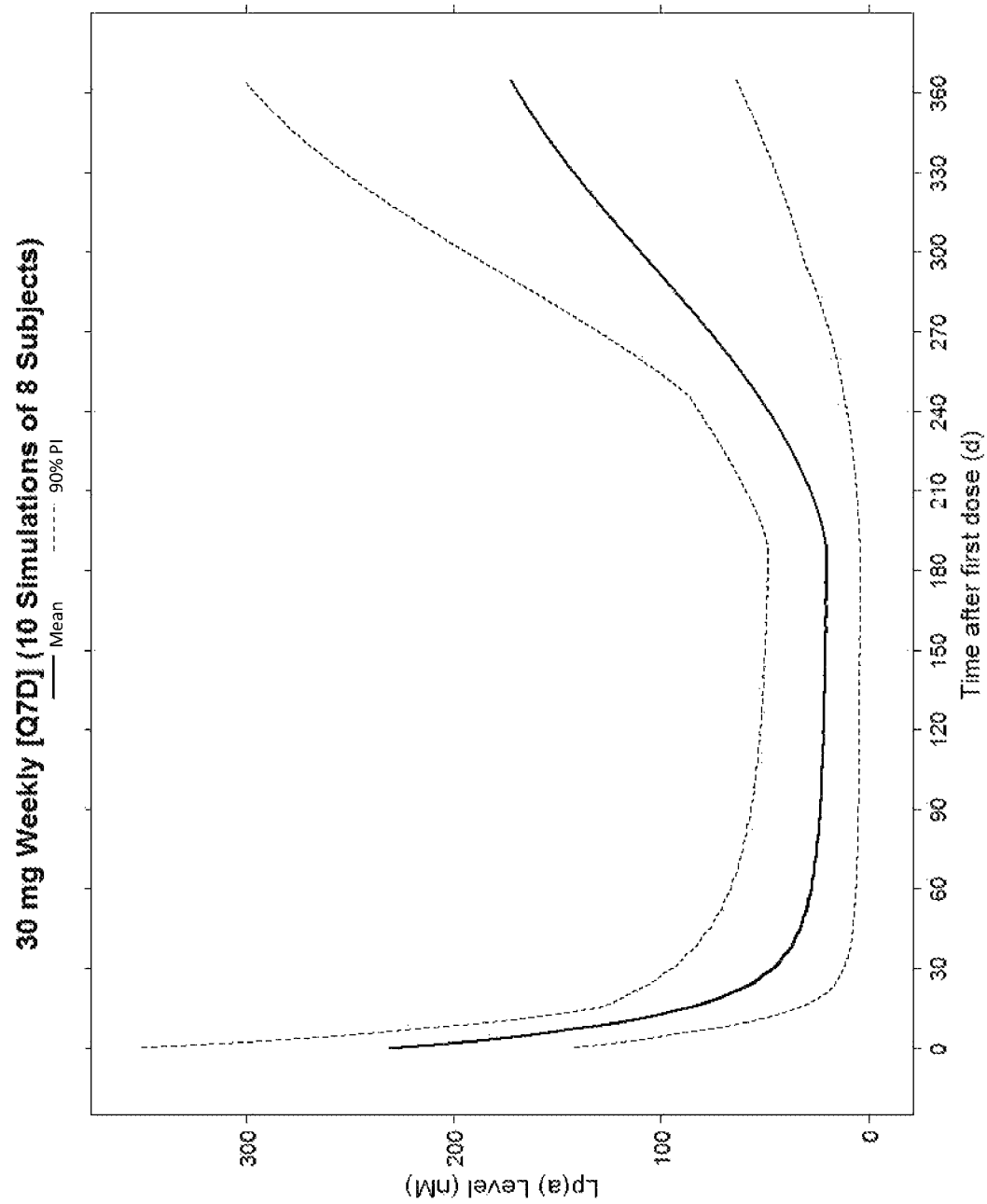

After completion of the phase 1 study described above, further modeling was performed to assess optimal clinical dose regimens for ISIS 681257.
Weekly Dosing
FIGS. 6A-D. Predicted Weekly Dosing Regimens. Charts are shown modeling the effect on Lp(a) by weekly administration of ISIS 681257 at doses of 5 mg (FIG. 6A), 10 mg (FIG. 6B), 20 mg (FIG. 6C), and 30 mg (FIG. 6D). The dark middle line represents the predicted dose, while the uppermost and lowermost lines represent the 90% Confidence Interval.
Monthly Dosing
FIGS. 5A-D. Predicted Monthly Dosing Regimens. Charts are shown modeling the effect on Lp(a) by monthly administration of ISIS 681257 at doses of 20 mg (FIG. 5A), 40 mg (FIG. 5B), 60 mg (FIG. 5C), and 80 mg (FIG. 5D). The dark middle line represents the predicted dose, while the uppermost and lowermost lines represent the 90% Confidence Interval.

Example 4: A Randomized, Double-Blind, Placebo-Controlled, Dose-Ranging Phase 2 Study of ISIS 681257 Administered Subcutaneously to Patients with Hyperlipoproteinemia(a) and Established Cardiovascular Disease (CVD)

The study described herein is to evaluate the safety, including tolerability, of ISIS 681257 and to assess the efficacy of different doses and dosing regimens of ISIS 681257 for reduction of plasma Lp(a) levels in patients with hyperlipoproteinemia(a) and established cardiovascular disease (CVD). CVD is defined as documented coronary artery disease, stroke, or peripheral artery disease. Patients must also have Lp(a) plasma level of ≥60 mg/dL. ISIS 681257 may provide therapeutic benefits to patients that have hyperlipoproteinemia(a) and established CVD.

Patient doses may be either 10 mg or 20 mg of ISIS 681257 administered once per week via subcutaneous injection for up to 52 weeks. Additional patient doses may be either 20 mg, 40 mg, or 60 mg administered once every 4 weeks via subcutaneous injection for up to 13 administrations. The primary endpoint is the percent change in plasma Lp(a) from baseline at the primary analysis time point for ISIS 681257 treatment groups compared to placebo. The primary analysis time point is at Week 25 for patients who received every 4-week dosing and at Week 27 for patients who received weekly dosing. Secondary empoints may comprise the effect of ISIS 681257 as compared to placebo at the primary analysis time point on any one of the following:

Percent change from baseline in LDL-C;
Proportion of patients who achieve plasma Lp(a)≤50 mg/dL;
Proportion of patients who achieve plasma Lp(a)≤30 mg/dL;
Percent change from baseline in apoB;
Percent change from baseline in OxPL-apo(a); and/or
Percent change from baseline in OxPL-apoB.

This study may reveal unexpectedly improved properties of ISIS 681257 when administered to human subjects with hyperlipoproteinemia(a) and established cardiovascular disease (CVD). Treatment with ISIS 681257 may produce reduction in Lp(a) in patients with hyperlipoproteinemia(a) and established cardiovascular disease (CVD). Treatment with ISIS 681257 may produce reduction in baseline LDL-C, baseline apoB, baseline OxPL-apo(a), and/or baseline OxPL-apoB.

The invention claimed is:

1. A method of treating a disease or condition in a human comprising administering to the human 75 mg to 85 mg of an oligomeric compound having the following structure:

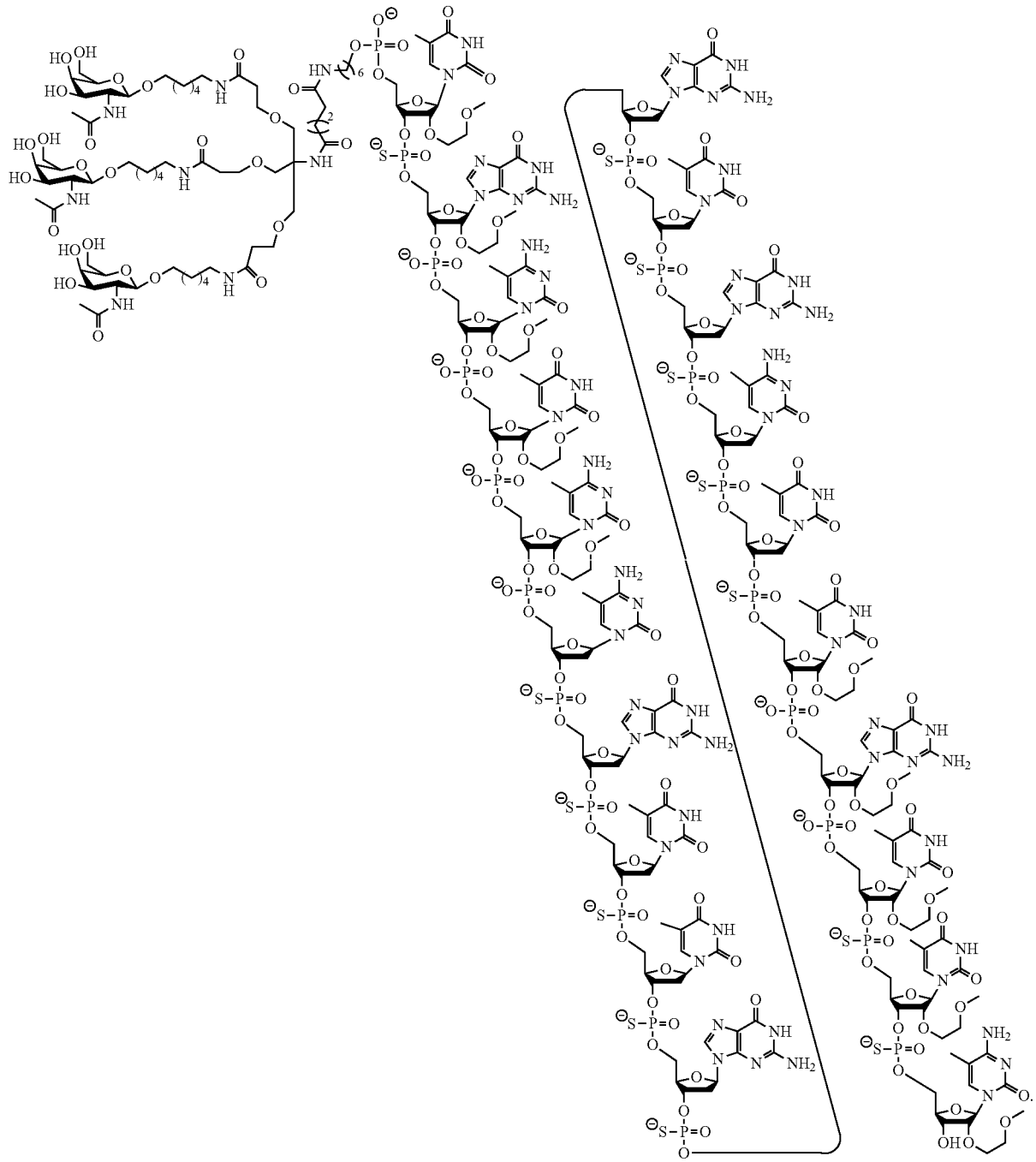

and thereby treating the disease or condition in the human.

2. The method of claim 1, wherein about 80 mg of the oligomeric compound is administered.

3. The compound of claim 1, wherein 80 mg of the oligomeric compound is administered.

4. The method of any of claims 1-3, wherein the disease or condition is cardiovascular disease.

5. The method of claim 1, wherein the oligomeric compound is administered as a sodium salt.

6. A method of treating a disease or condition in a human comprising administering to the human at least two separate doses of an oligomeric compound having the following structure:

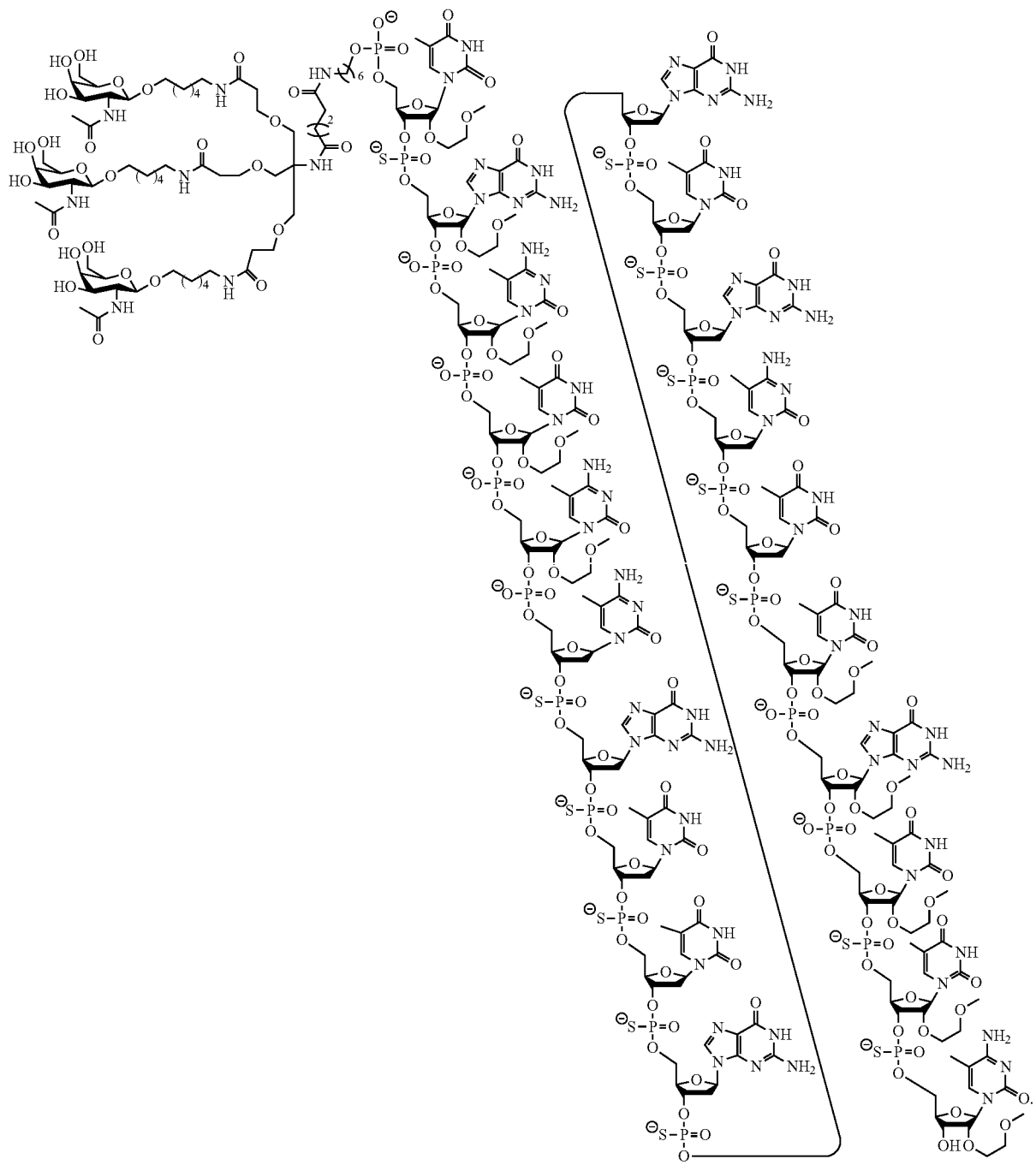

wherein each separate dose comprises 75 mg to 85 mg of the oligomeric compound; and wherein at least two doses are administered four weeks apart; and thereby treating the disease or condition in the human.

7. The method of claim 6, wherein each dose is about 80 mg of the oligomeric compound.

8. The method of claim 6, wherein each dose is 80 mg of the oligomeric compound.

9. The method of any of claims 6-8, wherein the disease or condition is cardiovascular disease.

10. The method of claim 6, wherein the oligomeric compound is administered as a sodium salt.

* * * * *